US008823482B2

(12) United States Patent
Singh et al.

(10) Patent No.: US 8,823,482 B2
(45) Date of Patent: *Sep. 2, 2014

(54) SYSTEMS USING MULTI-LAYER-MULTI-TURN HIGH EFFICIENCY INDUCTORS

(71) Applicant: NuCurrent, Inc., Chicago, IL (US)

(72) Inventors: Vinit Singh, Austin, TX (US); Jacob Babcock, Chicago, IL (US); Christine A. Frysz, Orchard Park, NY (US)

(73) Assignee: NuCurrent, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/797,629

(22) Filed: Mar. 12, 2013

(65) Prior Publication Data

US 2013/0208390 A1    Aug. 15, 2013

Related U.S. Application Data

(63) Continuation-in-part of application No. 13/233,569, filed on Sep. 15, 2011, which is a continuation-in-part of application No. 13/255,659, filed as application No. PCT/US2010/000714 on Mar. 9, 2010, now abandoned, application No. 13/797,629, which is a continuation-in-part of application No. 13/255,659, filed as application No. PCT/US2010/000714 on Mar. 9, 2010, now abandoned.

(60) Provisional application No. 61/158,688, filed on Mar. 9, 2009.

(51) Int. Cl.
*H01F 5/00* (2006.01)

(52) U.S. Cl.
USPC ............................................. 336/200

(58) Field of Classification Search
USPC .............................. 336/65, 83, 192, 200, 232
See application file for complete search history.

(56) References Cited

U.S. PATENT DOCUMENTS

| 2,911,605 A | 11/1959 | Wales, Jr. |
| 3,484,731 A | 12/1969 | Rich |
| 4,328,531 A | 5/1982 | Nagashima et al. |
| 4,494,100 A | 1/1985 | Stengel et al. |
| 4,959,631 A * | 9/1990 | Hasegawa et al. ............. 336/83 |
| 4,996,165 A | 2/1991 | Chang et al. |
| 5,237,165 A | 8/1993 | Tingley, III |
| 5,604,352 A | 2/1997 | Schuetz |
| 5,748,464 A | 5/1998 | Schuetz |
| 5,777,538 A | 7/1998 | Schuetz |
| 5,838,154 A | 11/1998 | Morikawa |
| 5,883,392 A | 3/1999 | Schuetz |
| 6,503,831 B2 | 1/2003 | Speakman |
| 6,664,863 B1 | 12/2003 | Okamoto et al. |
| 6,809,688 B2 | 10/2004 | Yamada |
| 6,924,230 B2 | 8/2005 | Sun et al. |
| 7,046,113 B1 | 5/2006 | Okamoto et al. |

(Continued)

*Primary Examiner* — Tuyen Nguyen
(74) *Attorney, Agent, or Firm* — McDermott, Will & Emery LLP

(57) ABSTRACT

A multi-layer, multi-turn structure for an inductor having a plurality of conductor layers separated by layers of insulator is described. The inductor further comprises a connector electrically connected between the conductor layers. The structure of the inductor may comprise a cavity therewithin. The structure of the inductor constructed such that electrical resistance is reduced therewithin, thus increasing the efficiency of the inductor. The inductor is particularly useful at operating within the radio frequency range and greater.

33 Claims, 29 Drawing Sheets

(56) References Cited

U.S. PATENT DOCUMENTS

| | | |
|---|---|---|
| 7,563,352 B2 | 7/2009 | Hubel |
| 7,713,762 B2 | 5/2010 | Lee et al. |
| 7,952,365 B2 | 5/2011 | Narita et al. |
| 8,056,819 B2 | 11/2011 | Rowell et al. |
| 2002/0105080 A1 | 8/2002 | Speakman |
| 2003/0119677 A1 | 6/2003 | Qiyan et al. |
| 2004/0000974 A1 | 1/2004 | Odenaal et al. |
| 2007/0023424 A1 | 2/2007 | Weber |
| 2008/0211320 A1 | 9/2008 | Cook et al. |
| 2009/0015266 A1 | 1/2009 | Narita et al. |
| 2009/0152542 A1 | 6/2009 | Lee et al. |
| 2009/0261936 A1 | 10/2009 | Widjaja et al. |
| 2011/0248891 A1 | 10/2011 | Han et al. |
| 2012/0235500 A1 | 9/2012 | Ganem et al. |
| 2012/0235634 A1 | 9/2012 | Hall et al. |

\* cited by examiner

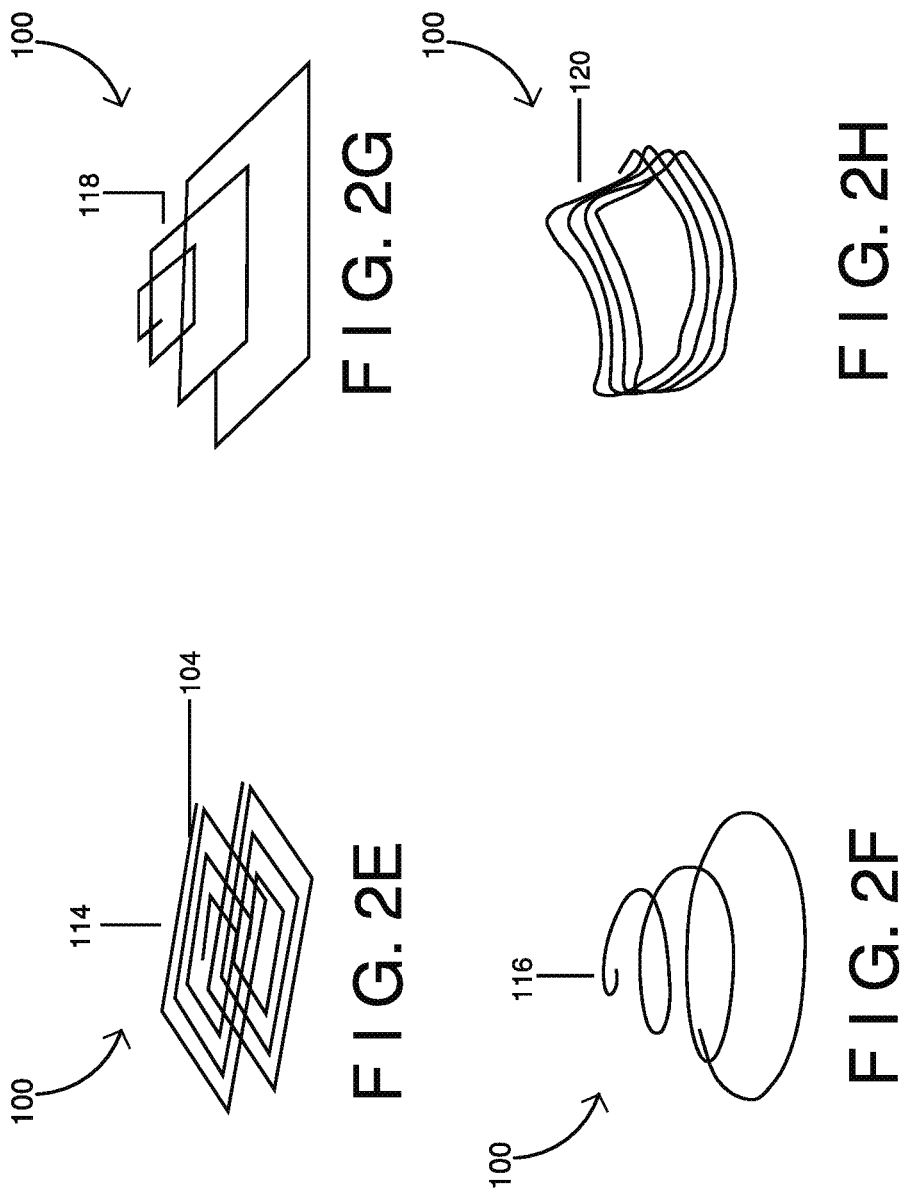

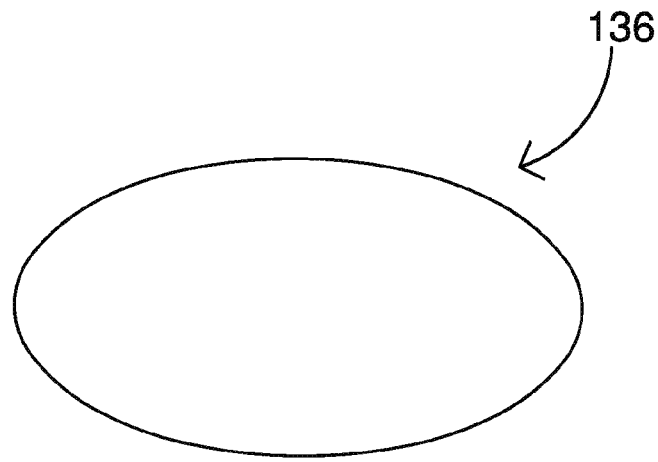
F I G. 4E
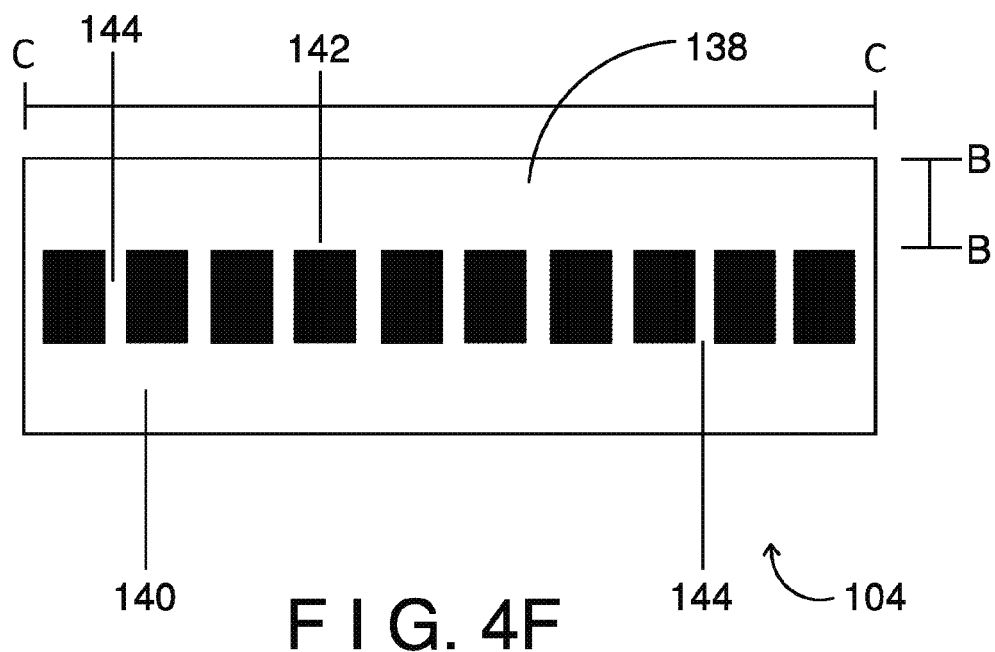
F I G. 4F

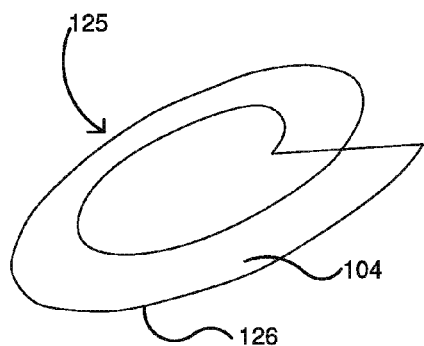 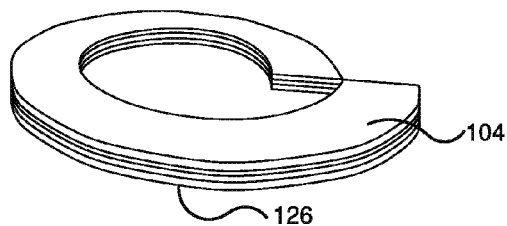
F I G. 7A    F I G. 7B
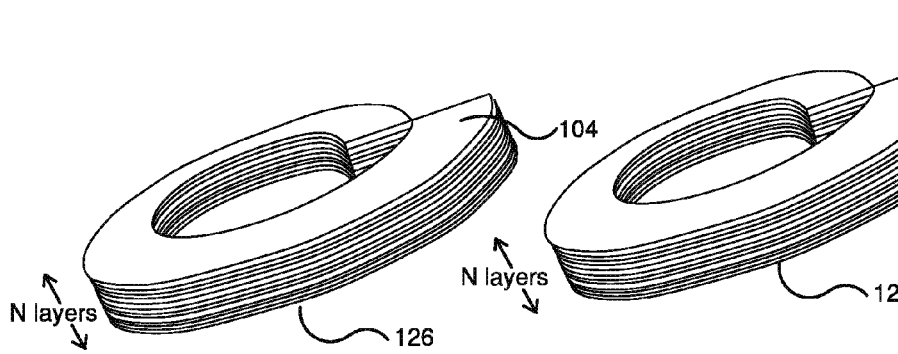 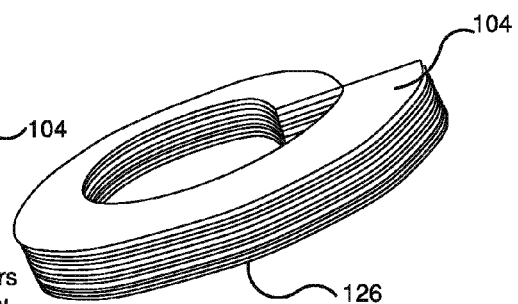
F I G. 7C    F I G. 7D

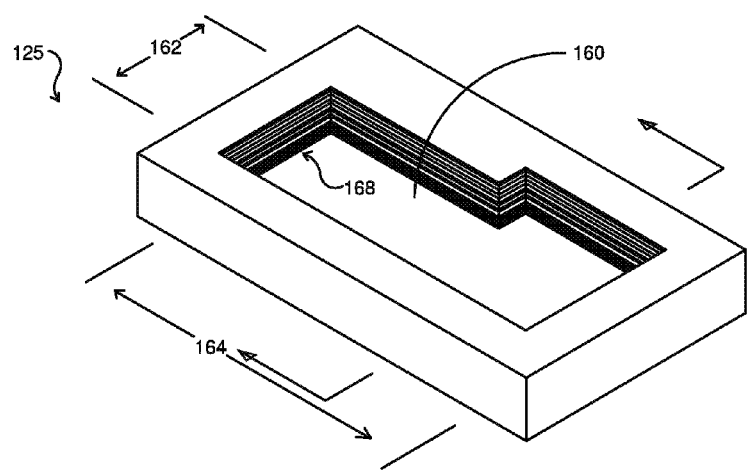
FIG. 13
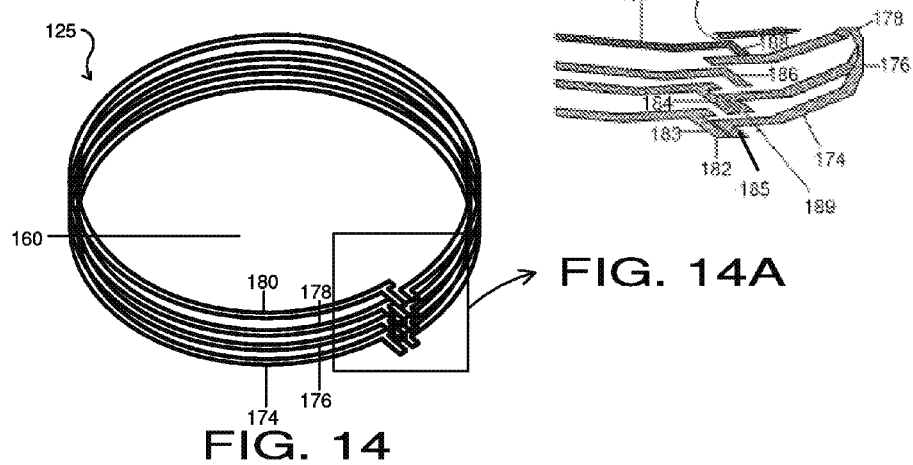
FIG. 14
FIG. 14A

SYSTEMS USING MULTI-LAYER-MULTI-TURN HIGH EFFICIENCY INDUCTORS

CROSS-REFERENCE TO RELATED APPLICATIONS

The present application is a continuation-in-part of U.S. application Ser. No. 13/233,569, filed Sep. 15, 2011, which is a continuation-in-part of U.S. application Ser. No. 13/255,659, filed Sep. 9, 2011, which is a 371 application of International Application No. PCT/US2010/000714, filed Mar. 9, 2010, which is a nonprovisional of U.S. Provisional Application No. 61/158,688, filed Mar. 9, 2009, the disclosures of which are entirely incorporated herein by reference.

The present application is a continuation-in-part of U.S. application Ser. No. 13/255,659, filed Sep. 9, 2011, which is a 371 application of International Application No. PCT/US2010/000714, filed Mar. 9, 2010, which is a nonprovisional of U.S. Provisional Application No. 61/158,688, filed Mar. 9, 2009, the disclosures of which are entirely incorporated herein by reference.

The present patent application also hereby incorporates by reference the entire contents of U.S. patent application Ser. No. 13/233,538, filed Sep. 15, 2011; U.S. patent application Ser. No. 13/233,624, filed Sep. 15, 2011; U.S. patent application Ser. No. 13/233,663, filed Sep. 15, 2011; U.S. patent application Ser. No. 13/233,686, filed Sep. 15, 2011; U.S. patent application Ser. No. 13/233,729, filed Sep. 15, 2011; U.S. patent application Ser. No. 13/233,735, filed Sep. 15, 2011; and U.S. patent application Ser. No. 13/233,751, filed Sep. 15, 2011.

BACKGROUND OF THE INVENTION

1. Field of the Invention

The present invention generally relates to electrical circuit components, and more specifically, to the design, operation and method of manufacture of an efficient inductor and related systems thereof.

2. Prior Art

Inductors have been extensively utilized in electrical circuits for many years dating back to the late 1800s. Inductors are utilized in just about every electrical circuit and they play a vital role in the operation of numerous electronic devices from modern televisions to satellite communication systems. There are two common types of prior art inductors, the first type are wire wound inductors, and the second type are ceramic based inductors. Wire wound inductors have historically been constructed of a metal coil that is wrapped around a core of air, paramagnetic, or ferromagnetic material. Ceramic-based inductors are typically multilayer, film or wire-wound technologies, each having features that provide characteristics suitable for various applications.

In an inductor, electric current travels through the metallic coil generating a magnetic flux that is proportional to the amount of electric current. A change in electrical current elicits a corresponding magnetic flux proportional to the amount of current, which in turn, generates an electromotive force (EMF), measured in volts, that opposes the change in current. Inductance is a measure of the amount of EMF generated per unit change in current. For example, an inductor with an inductance of 5 henries produces an EMF of 5 volts when the current through the inductor changes at a rate of 5 amperes per second.

A pure or "ideal inductor" is an inductor that is one hundred percent efficient. Such an ideal inductor does not dissipate or radiate energy. However, inductors utilized in electrical circuits are not theoretical ideal inductors, but rather, are "real inductors", in that they have internal losses that dissipate or radiate energy and contribute to the overall inefficiency of the inductor. Energy loss within an inductor is generally due to internal electrical resistance which is generally the result of the traditional structure and design of an inductor, for example, wherein a coil is wrapped around a core of air or some material or wherein a coil structure is associated with a ceramic substrate.

Specifically, the electrical resistance within an inductor is generally caused by the cumulative effects of the electrical resistance of the coil structure that is either a wire wrapped around a core material or a trace, film or mounted wire on a ceramic substrate. This internal loss becomes more pronounced as the operating frequency is increased. At high frequencies, particularly at radiofrequencies (RF) and greater, inductors of the prior art, typically have higher electrical resistance and other losses. In addition to causing power loss, in inductance circuits this can reduce the quality factor (Q factor) of the inductor and the electrical circuit, broadening the bandwidth. In prior art ceramic based inductors, for example, Q factor values at of about 5 to about 30 are generally achieved at a given frequency. Prior art wire wound inductors with either air or ferrite cores have Q values on the order of 50 to 100. Furthermore, the Q values of these prior art inductors significantly degrade with increasing operating frequency.

The multi-layer, multi-turn inductor of the present invention performs at greater efficiencies in a similar volume and at similar efficiencies in a substantially smaller volume. In particular, the inductor of the present invention performs at greater efficiencies, particularly at RF frequencies and greater. In operation, the multi-layer, multi-turn inductor of the present invention generally has a Q factor that is about 20 to 30 percent greater than the inductor designs of the prior art.

The relatively low quality factor of these inductors is mainly due to higher resistive losses caused by a phenomenon known as the "skin effect." Generally, skin effect is the tendency of an alternating electric current (AC) to distribute itself within a conductor such that the current density is more predominant near the surface of the conductor with the remaining conductor body 'unused' relative to electrical current flow. The remaining conductor body is 'unused' relative to electrical current flow because the current density typically decays with distance therewithin away from the surface of the conductor. The electric current flows mostly near the surface, and is referred to as the "skin" of the conductor. The depth at which the current decays to about 37% of the magnitude than at the surface is called the "skin depth." The "skin depth" then defines the electrical current cross-sectional area that is carries most of the current (is active) in the conducting wire of an inductor, whether the inductor wire is wire that is wound around a core material, or a wire that is a trace, a film or a mount on a ceramic substrate.

In inductors, particularly those operating in the RF frequency range and above, the skin effect phenomenon generally causes energy loss as current flows through the wire of the inductor and circuit. Higher resistive loss at high frequencies is a problem faced by most electronic devices or appliances. Skin effect becomes more prevalent when operating frequency increases. With higher frequencies, current that normally flows through the entire cross section of the wire comprising the inductor becomes restricted to its surface. As a result, the effective resistance of the wire is similar to that of a thinner wire rather than of the actual diameter through which the current could be distributed. A wire exhibiting tolerable resistance for efficient performance at low frequency transitions into a wire of unacceptable resistance at high frequency. The transition from tolerable to unacceptable resistance translates into inefficient lower quality factor values of the inductor and overall electrical circuit. Additionally, current inductor designs do not resolve these inefficiencies, and, in some cases, exacerbate the inefficiencies of the electrical circuit, particularly at high RF frequencies. Although not exhaustive, typical applications limited by current inductor technology include, for example, radio frequency identification (RFID), battery charging and recharging, telemetry, sensing, communication, asset tracking, patient monitoring, data entry and/or retrieval, induction heating, electromagnetic field generation, RF matching, RF chokes, RF MEMs, electronic switching, interference filtering, oscillators, amplifiers, induction heating, microwave circuits, magnetic resonance imaging, and the like. Further, these inductor fabrication techniques are relatively complex and are cost prohibitive.

In RFID applications, such as supply chain management, product authenticity, and asset tracking, there is a need to increase read range, increase read rates, improve system reliability and improve system accuracy. At high frequency for example, read range is at most three feet which is generally insufficient for pallet tracking. Ultra high frequency readers enable greater read distances of eight to ten feet, however, they introduce other performance issues like signals that are reflected by metal or are absorbed by water, or display unreadable, null spots in read fields. Increased read range requires concentrated power to facilitate reflecting back the signal for better performance, hence, a more efficient structure could help solve these issues.

In applications requiring efficient low loss coils which need to maintain inductance under harsh conditions, conventional wire-based inductors could be deformed. It is well known that any deformation of the wire cross-section will lead to a change in inductance and possibly resistance, which in turn will change the resonance frequency of the inductor and consequently may increase overall system resistance and degrade system performance. Improved methods of manufacturing these types of structures that reduce the potential for compromising deformation could eliminate this problem. The present teachings include methods of manufacture that include both rigid structure designs and flexible structure designs.

Litz wires were developed, in part, in an attempt to address the issues discussed above. However, Litz wires are generally insufficient for use in high frequency applications, and are therefore generally not useful in applications having operating frequencies above about 3 MHz. Furthermore, inductors constructed with Litz wire tend to deform under physical stresses and deteriorate when exposed to harsh environmental conditions. A Litz wire is a wire consisting of a number of individually insulated magnet wires twisted or braided into a uniform pattern, so that each wire strand tends to take all possible positions in the cross-section of the entire conductor. This multi-strand configuration or Litz construction is designed to minimize the power losses exhibited in solid conductors due to "skin effect" and "proximity effect". Litz wire constructions attempt to counteract this effect by increasing the amount of surface area without significantly increasing the size of the conductor. However, even properly constructed Litz wires exhibit some skin effect due to the limitations of stranding. Wires intended for higher frequency ranges generally require more strands of a finer gauge size than Litz wires of equal cross-sectional area, but these higher frequency wires are composed of fewer and larger strands.

Further, the highest frequency at which providers of Litz wires offer configurations capable of improving efficiencies is about 3 MHz. There is currently no solution for applications with operating frequencies beyond this 3 MHz maximum frequency limit. Additionally, there is currently no solution that improves efficiency in a given size or provides similar efficiency in a smaller size.

Hence a need exists for an improved high efficiency design and method of manufacture that reduces the intrinsic resistive losses of the inductor structure, and in particular reduces intrinsic resistive losses of the inductor at high frequencies to achieve high quality factors.

SUMMARY OF THE INVENTION

The teachings herein alleviate one or more of the above noted problems of higher resistive losses at high frequencies resulting in lower quality factors by utilizing the multi-layer wire concept to increase the area of conductance within an inductor structure. The multi-layer wire configuration results in a reduction of resistance loss and an increase in the qualify factor of the inductor structure and resulting electrical circuit. The present teachings apply to the structure and design of a novel inductor for incorporation within electrical circuits. Most notably electrical circuits that operate within and above the radio frequency range of at least 3 kHz.

One aspect of the present teachings is of an inductor wherein resistive losses within the inductor are minimized by maximizing useful conductor cross-sectional area in a wire cross section. In one embodiment, the inductor mitigates the unwanted high frequency skin effect by creating the following structure: by introducing non-conducting or poorly conductive dielectric layers within its wire, resulting in a structure that comprises layers of conducting material alternating with layers of non-conducting or poorly conducting material. The structure effectively provides an increased number of surfaces each with its characteristic skin depth and all electrically, or otherwise, connected. The skin depth may range from approximately one-half of the conductor depth to about equal to the conductor depth. The conductor depth may be in the range of skin depth to twice the skin depth. However, depending on the available technology, costs, and application, the conductor depth may be as large as twenty times or more the skin depth.

The inductor typically includes a coil having at least one turn wherein the coil is made up of a multi-layer wire. In some instances, the desired inductance may be achieved with the coil having a partial turn. For example, the coil or segment of a coil, such as an arc of a circle or side of a polygon, may be positioned such that it does not complete a full turn or revolution. A fraction or partial turn may be used in addition to a set of full turns to achieve a specific inductance value. Furthermore, the conductor layers and/or insulative dielectric layers may be composed of differing materials.

In another embodiment, the desired inductance may be achieved wherein the multi-layer wire comprises different materials in at least two layers. For example, the coil or a segment of a coil, may comprise a thin layer of conductive material, i.e., a conductive trace that is deposited on a surface of one or multiple insulative and/or conductive layers. Furthermore, different materials may be used throughout the MLMT inductor structure. For example, one insulative layer may comprise a different insulative material than another insulative layer. Likewise, a conductive layer may comprise a different conductive material than another conductive layer. Such use of different conductive and insulative materials, as will be discussed further, may be used to modify or tune the inductance and performance efficiency of the MLMT inductor at different operating frequencies. In addition, the use of such materials, particularly insulative materials, may also be used to control and minimize heat that may be generated by the MLMT inductor, particularly at increased frequencies.

The desired inductance can also be achieved by the combination of turns, or partial turns, with the different material or materials that comprise the coil or segment of the coil. Hence, it is left to the designer to use several layers and/or multiple conductive traces, all of which are connected in a manner to specifically achieve an application need or an application use specification.

In another embodiment, the desired inductance may be achieved or tuned using specific non-conducting or poorly conducting materials, such as semi-conducting materials, to separate the conductive layers, or it may be achieved by creating a cavity within the layer or layers and filling it with specific materials that contribute to the overall inductance of the final inductor component. The multi-layer wire may include a first and second conductive layer separated by a layer of insulating material. The conductive layers may have substantially the same thickness and/or depth, wherein the thickness and/or depth may be in the range of skin depth to twice the skin depth. However, depending on the available technology, costs, and application, the conductor thickness and/or depth may be as large as twenty times or more the skin depth. Each conductive layer may be electrically connected to each other using at least one method of interconnect, such as but not limited to a via, a solder, a tab, a wire, a pin, or a rivet.

One purpose of the non-conducting layer is to insulate two different conducting layers. The most basic design of the non-conducting layer would ideally be as thin as the manufacturing process practically permits, while still providing sufficient insulating properties. For example, in PCB technology, the thickness of layers is dictated by the "core thickness" and the prepreg thickness. In another design, the thickness of the non-conducting layer is selected to modify the electrical behavior of the structure. In another embodiment, the thickness of the non-conducting layer may be modified to minimize performance degradation due to "proximity effects." In yet another embodiment, the conductors on each layer may be staggered from subsequent layers to reduce "proximity effects." In another embodiment, the conductor widths may be different from each other to account for the proximity effect. It is possible that all the above mentioned embodiments may be implemented simultaneously in the same structure, or only a subset of the embodiment may be implemented.

The multi-layer, multi-turn inductor of the present invention generally has a quality factor that is greater than inductors of prior art designs and constructions. While the quality factor varies with operating frequency and inductance, the quality factor of the multi-layer, multi-turn inductor of the present invention may range from about 5 to over 100 or more. For example, a multi-layer, multi-turn inductor of a surface mount design, having a foot print of about 1.6 mm by 0.8 mm, and operating at about 100 MHz may have a quality factor of about 10, more preferably of about 20 and most preferably of about 40 or more.

In another example, an inductor used in wireless power applications having a diameter of about 2.5 cm and an inductance of about 48 uH, operating at a frequency between about 110 to 205 KHz may have a QF of about 15, more preferably of about 25 and most preferably of about 45 or greater.

In a further example, an inductor used in a high frequency application having a footprint of about 6.4 mm by about 5.0 mm and an inductance about 35 nH, operating at a frequency of about 150 MHz may have a QF of about 135, preferably of about 150 and most preferably of about 190 or greater.

In another example, an inductor used in a wireless communication circuit having a footprint of about 1 mm by 0.5 mm and an inductance of about 1.6 nH, operating at a frequency of about 250 MHz may have a QF of about 20, more preferably of about 30 and most preferably of about 45 or greater.

In yet another example, an inductor used in a wireless power or RFID application having a footprint of about 4.8 cm by about 4.8 cm and an inductance about 5 uH, operating at a frequency of about 13.56 MHz may have a QF of about 30, more preferably of about 70, and most preferably of about a 100 or greater.

It will be apparent to those skilled in the art that systems requiring two or more inductors may either have inductors with equal and even similar quality factors. Also, it will be apparent to one skilled in the art that systems requiring two or more inductors may utilize inductors where one inductor has a quality factor substantially different from the other. The quality factor selection for each inductor will depend on the application, the design specification for each and the intended use of each inductor. Additionally, it will be apparent to one skilled in the art that the quality factor of an inductor may be dependent on the environment in which it is used, so, for example, an inductor that has a quality factor of 20 in air, may only have a quality factor of 10 when implanted in human or animal tissue. In any given environment, the MLMT inductor structure described herein should outperform traditional inductors.

It is important to note that inductors used in high-frequency applications often exhibit higher losses due to a phenomenon called the skin effect. Skin effect reduces conductive cross-sectional area, thereby increasing the resistance of a structure. The increased resistance, in turn, causes higher energy losses in the component. There are several disadvantages of the higher energy losses. For example, higher energy losses may cause heating of a component. In some cases, component heating may present a safety risk, could damage equipment, or the like. To resolve overheating, sometimes costly mechanisms for heat management are incorporated. In other situations, high energy losses substantially degrade efficiency. This is particularly undesirable in mobile applications where extended battery life is needed. In the area of wireless power transfer, particularly wireless power transfer utilizing magnetic fields, inductive antennas with high energy losses result in limited wireless range, transmission dependence on orientation, and lower power transfer to the point of repeated unsuccessful transmissions.

As a result, the reduction of losses in the wire and the significantly reduced internal resistance of the inductor could enable high efficiency, compact electronic systems that consume less energy, have longer run time and simplify operation without compromising events like overheating, undesirable restrictions for successful transmission like orientation or insufficient power transfer.

In one example, there is disclosed a structure for an inductor that may be utilized in a variety of non-limiting electronic circuits. The structure is designed to produce an inductance with reduced internal loss, particularly reduced electrical resistance at RF ranges and above. In addition, the structure may be designed such that it is capable of selectively tuning the inductor structure or adjusting its inductance and/or quality factor to meet application and/or environment. Furthermore, the structure may be capable of transmitting and/or receiving a combination of electrical energy, electromagnetic energy, electrical power and electronic data together or separately.

The structure may comprise a plurality of conductor layers, an insulator layer separating each of the conductor layers, and at least one connector connecting two or more of the conductor layers. Each of the plurality of conductor layers may have at least one turn and may further be placed in a parallel orientation. Alternately the layers may be arranged in a perpendicular or an angled relationship. Each conductor layer may be formed from an electrically conductive material. The electrically conductive material may be comprised of copper titanium, platinum and platinum/iridium alloys, tantalum, niobium, zirconium, hafnium, nitinol, cobalt-chromium-nickel alloys, stainless steel, gold, a gold alloy, palladium, carbon, silver, a noble metal or a biocompatible material and any combination thereof.

The conductor layer may have a cross-sectional shape, such as, but not limited to, a curved cross-section, a circular cross-section, a rectangular cross-section, a square cross-section, a triangular cross-section, an elliptical cross-section or a trapezoidal cross-section. The connector connecting the conductor layers may be but is not limited to a via, a solder, a tab, a wire, a pin, or a rivet. The structure may have structural shape, such as but not limited to a circular solenoidal configuration, a square solenoidal configuration, a circular spiral configuration, a square spiral configuration, a rectangular configuration, a triangular configuration, a circular spiral-solenoidal configuration, a square spiral-solenoidal configuration, and a conformal solenoid configuration. Other configurations may be used to modify the electrical properties of the structure.

Electrical resistance in the multi-layer multi-turn inductor structure of the present invention may be reduced when an electrical signal is induced in the inductor at a frequency. The frequency may be selected from a frequency range from about 3 kHz to about 10 GHz. Further, the frequency may be a frequency band that ranges from or is within about 3 kHz to about 10 GHz. The electrical signal may be an electrical current, an electrical voltage, a digital data signal or any combination thereof.

The inductor may comprise a plurality of conductors, each conductor having a conductor length, a conductor height, a conductor depth, and a conductive surface having a skin depth at the operating frequency/frequencies. The skin depth may range from approximately one-half of the conductor depth to about equal to the conductor depth. The conductor depth may be in the range of skin depth to twice the skin depth. However, depending on the available technology, costs, and application, the conductor depth may be as large as twenty times or more the skin depth. The plurality of conductor layers may have at least one turn. Further, each of the plurality of conductor layers may or may not have substantially the same conductor length, conductor height, or conductor depth. The conductor layers may be formed from an electrically conductive material.

The electrically conductive material may be comprised of copper, titanium, platinum, platinum/iridium alloys, tantalum, niobium, zirconium, hafnium, nitinol, cobalt-chromium-nickel alloys, stainless steel, gold, a gold alloy, palladium, carbon, silver, a noble metal or a biocompatible material and any combination thereof.

The plurality of conductors may be arranged to form an insulator body. The insulator body may have an insulator body length, an insulator body width and an insulator body depth. When an electrical signal is induced within the insulator body, the electrical signal propagates predominately through the skin depth. The electrical signal may be an electrical current, an electrical voltage, a digital data signal or any combination thereof.

The plurality of conductors in the insulator may comprise a first conductor layer and a second conductor layer separated by an insulator layer wherein the first conductor layer is connected to the second conductor layer or more by at least one connector. The conductor may have a cross-sectional shape, such as but not limited to a circular cross-section, a rectangular cross-section, a square cross-section, a triangular cross-section, or an elliptical cross-section. The insulator may have a structural shape such as but not limited to a circular solenoidal, a square solenoidal configuration, a circular spiral configuration, a square spiral configuration, a rectangular configuration, a triangular configuration, a circular spiral-solenoidal configuration, a square spiral-solenoidal configuration, or a conformal solenoid configuration.

There is also disclosed a circuit for selectively adjusting or tuning the output or performance parameters of the inductor. The circuit may be housed within the inductor body or provided external to the inductor. Such a circuit may be designed to selectively adjust the inductance and/or the quality factor of the inductor. In addition, the resonance frequency, the impedance or the quality factor of the electronic circuit within which the inductor is connected to. The circuit may be designed to adjust the internal resistance within the inductor, thereby adjusting the inductor's quality factor. Such a circuit may also be used to selectively adjust the inductance output of the inductor. The circuit may be triggered or activated manually or automatically, either through a physical or electrical means such as by a multitude of stimuli, including but not limited to an electrical signal or change in its surrounding environment such as a change in temperature and/or pressure. For example, the quality factor of the inductor may be selectively adjusted by changing the internal resistance parameters when the circuit is triggered by a change in external temperature.

Circuits at high frequencies extensively use additional passive elements such as inductors, capacitors, and the like. Some examples of such circuit configurations include but are not limited to band pass, high pass and low pass filters; mixer circuits (e.g., Gilbert Cell); oscillators such as Colpitts, Pierce, Hartley, and clap; and, amplifiers such as differential, push pull, feedback, and radio-frequency (RF). Specifically, inductors are used in matching and feedback in low noise amplifiers (LNAs) as a source degeneration element. Lumped inductors are also essential elements in RF circuits and monolithic microwave integrated circuits (MMICs). Lumped inductors are used in on-chip matching networks where transmission line structures may be of excessive length. Often, they are also used as RF chokes allowing bias currents to be supplied to circuits while providing broad-band high impedance at RF frequencies and above. RF MEMS switches, matching networks and varactors that are ideal for reconfigurable networks, antennas and subsystems also need high Q inductors. Note, passive circuit element and lumped element, such as lumped inductor, may be used interchangeably with passive circuit element being the broader term. The passive circuit element may be an inductor, a capacitor, a resistor or just a wire. In nearly all the above mentioned circuit examples, not meant to be limiting, it is desired that the passive components are minimally lossy.

A benefit of the multi layer multi turn (MLMT) structure of the inductor of the present invention is its flexibility of design. The MLMT structure affords the ability to achieve a wide range of inductance values with high reliability and efficiency, for a wide range of applications. In general, design specifications are created for a particular application need(s) and/or performance requirement. For example, a particular application may require an inductor having a specific self-inductance, mutual inductance with another inductor, or both. Such a design specification may also limit size, demand a particular maximum resistance, or both which may not be able to be achieved by a prior art inductor.

In particular, the electrical efficiencies of the present invention, achieved by the MLMT structure, provide an electrical component designer the ability to meet or exceed particular application design specifications that cannot be achieved by today's inductors. In particular, the MLMT structure of the present invention provides an efficient, highly reliable inductor that can operate at increased frequencies in a smaller size as compared to the prior art. Furthermore, the inductance of the present invention may be designed to be tunable to specific inductance values while in operation.

Given circuits at high frequencies extensively use passive elements such as inductors and capacitors, an embodiment is given using but is not limited to an inductor. Specifically considering an inductor, the designs should be such that maximum Q is attained while achieving the desired inductance value. In other words, the resistive loss in the inductor needs to be minimized. Depending on the frequency of operation, available area on the substrate, the application and the technology, the inductor can be implemented as, but not limited to, a TEM/transmission line, a conductive loop or conductive loops, or a spiral/solenoid/combination structure of several shapes, for example, but not limited to, a circle, a rectangle, an ellipsoid, a square, or an irregular configuration. All these embodiments, not meant to be limiting, may be realized using the multi-layer structure in the present invention.

In another example, an inductor as part of a larger circuit is discussed. An inductor is a device or a system that stores energy in proximal magnetic fields at a specific frequency, frequencies, or frequency band(s), called the inductance frequency, frequencies, or frequency band(s). At the inductance frequency, frequencies, or frequency band(s), there is minimum electrical resistance to oscillation. In the context of electrical circuits, there is minimum electrical resistance at an optimum inductance frequency, frequencies, or frequency band(s). The MLMT structure of the present invention may act as an inductor under two fundamental conditions: (1) When the MLMT structure is designed to resonate at a specific frequency, frequencies, or frequency band(s), in its environment without any additional electrical components as a self-resonator; (2) When the MLMT structure is designed to resonate at a specific frequency, frequencies, or frequency band(s), in its environment in combination with other components (for example, but not limited to, a capacitor, a capacitor bank, a capacitor and/or an inductor network). Thus, the inductor may be part of a larger circuit, and the inductance behavior may be designed to occur at a frequency, frequencies, or frequency band(s), or at a frequency, frequencies, or frequency band(s) with a certain bandwidth or certain bandwidths. Additional components (e.g., resistance) may also be added to alter the bandwidth(s).

Accordingly, it is the unique arrangement of the conductive and insulative layers, the specific design of these layers, i.e., length, width, material, and, in particular, thickness, coil segmentation, and electrical connection, that results in its higher efficiency in a similar or smaller size/volume than the prior art. This outcome is evidenced by quality factors that are more than two times higher than the prior art. In addition, there is disclosed a method for manufacturing the multi-layer, multi-turn inductor structure of the present invention. The method of manufacture creates a structure that is capable of providing inductance within an electrical circuit, particularly at RF frequencies and greater.

The method may comprise the steps of creating a plurality of conductor layers having an insulator between each of the conductor layers and forming at least one connection between two of the plurality of conductors. The connector connecting the conductor layers may be but is not limited to a via, a solder, a tab, a wire, a pin, or a rivet. The conductor layers may be created by depositing through a mask. Alternatively, the conductor layer may be created by etching excess material away. In either case, the step of creating a plurality of conductor layers having an insulator between each of the conductor layers may further include the steps of placing a first conductive layer on top of a second conductive layer and separating the first conductive layer from the second conductive layer with a first insulator. Further, the step of forming at least one connection between two of the plurality of conductors may include the steps of connecting at least two of the conductive layers comprising but not limited to a via, a solder, a tab, a wire, a pin, or a rivet. The conductor layers may be formed from an electrically conductive material. The electrically conductive material may be comprised of copper, titanium, platinum and platinum/iridium alloys, tantalum, niobium, zirconium, hafnium, nitinol, cobalt-chromium-nickel alloys, stainless steel, gold, a gold alloy, palladium, carbon, silver, a noble metal or a biocompatible material and any combination thereof.

There is also disclosed a method for operating the multi-layer, multi-turn inductor structure of the present invention to provide inductance within a multitude of electronic circuits. The method comprises the steps of providing a structure that is capable of providing an inductance with an increased quality factor. In addition, the method provides the steps of providing a structure that is capable of selectively adjusting or tuning the inductor wherein the inductance output and/or the inductor quality factor may be changed manually or automatically, such as through an electrical means.

The method comprises the steps of providing a plurality of conductors, each conductor having a conductor length, a conductor height, a conductor depth, and a conductive surface having a skin depth at the operating frequency/frequencies. The skin depth ranges approximately one-half of the conductor depth to about equal to the conductor depth. The conductor depth may be in the range of skin depth to twice the skin depth. However, depending on the available technology, costs, and application, the conductor depth may be as large as twenty times or more the skin depth. The plurality of conductors may be arranged to form an inductor body having an inductor body length, an inductor body width and an inductor body depth; and, inducing an electrical signal in at least one of the plurality of conductors such that the electrical signal propagates through the conducting surface of the skin depth. The electrical signal may be an electrical current, an electrical voltage, a digital data signal or any combination thereof.

The method may also include the step of providing a second plurality of conductors, each of the second conductors having a second conductor length, a second conductor height, a second conductor depth, and a second conductive surface having a second skin depth wherein the plurality of second conductors are arranged to form a second insulator body having a second insulator body length, a second insulator body width and a second insulator body depth. When an electrical signal is propagated through the inductor body, the electrical signal propagates through the conducting surface and further induces an electrical signal through the second inductor body, and the induced electrical signal propagates through the second conducting surface.

The plurality of conductors may comprise a first conductor layer and a second conductor layer separated by an insulator layer wherein the first conductor layer is connected to the second conductor layer by at least one connector. Further, the at least one connection connecting at least two of the conductive layers comprises but is not limited to a via, a solder, a tab, a wire, a pin, or a rivet. The conductor may have a cross-sectional shape not limited to a circular cross-section, a rectangular cross-section, a square cross-section, a triangular cross-section, and an elliptical cross-section. The plurality of conductor layers may have at least one turn and each of the plurality of conductor layers may have substantially the same conductor length, conductor height, and conductor depth. The conductor layer may be formed from an electrically conductive material. The electrically conductive material may be comprised of copper titanium, platinum and platinum/iridium alloys, tantalum, niobium, zirconium, hafnium, nitinol, cobalt-chromium-nickel alloys, stainless steel, gold, a gold alloy, palladium, carbon, silver, a noble metal or a biocompatible material or any combination thereof.

The inductor may have a structural shape not limited to a circular solenoidal configuration, a square solenoidal configuration, a circular spiral configuration, a square spiral configuration, a rectangular configuration, a triangular configuration, a curved configuration, a trapezoidal configuration, a circular spiral-solenoidal configuration, a square spiral-solenoidal configuration, and a conformal solenoid configuration. Accordingly, the present invention differs substantially from the prior art in several ways. Unlike the prior art, including Litz wires, the present invention is optimizable for operation at frequencies up to several hundred MHz. Also, unlike the prior art, especially Litz wires, the present invention is producible by using integrated fabrication technologies such as PCB, Co-fired Ceramic (LTCC and HTCC), flex circuit technology, semiconductor technology, and the like. Hence, the present invention itself and its method of manufacture provide for integratable inductor structures that are robust, are reproducibly manufacturable and that perform as required repeatably.

In addition to the differences noted above, the present invention also offers a lower cost alternative to the prior art such as Litz wires. Since fabrication of the inductor structure of the present invention is in-situ it requires only one step to create. Litz wire fabrication on the other hand uses two steps in its fabrication. More notably, however, is that the fabrication process for the present invention allows for dynamic tuning of the MLMT inductor or the inductive structure. The multilayer fabrication process, in particular, provides for inclusion of active devices operating as switches. These switches may actively connect or disconnect layers. Judicious selection and use of these switches may create unique and different inductance values, resistance values or both. Additional components introduced to a circuit, for example, may increase overall system losses. In particular embodiments of the present invention, however, tunability becomes possible. Tunability permits losses to be kept below those typical for conventional prior art inductors.

Further, the multilayer structure allows fabrication of in-situ LC circuits. By appropriately inserting a dielectric material in a formed cavity and/or depositing a large area metal trace, increased capacitance may be obtained.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 2E illustrates an embodiment of an inductor in a multi-layer square.

FIG. 2F illustrates an example of an inductor in a circular conical-solenoidal (or pyramidal-solenoidal) configuration.

FIG. 2G illustrates an embodiment of an inductor in a square conical-solenoidal (or pyramidal-solenoidal) configuration.

FIG. 2H illustrates an embodiment of an inductor in a conformal solenoid configuration.

FIG. 4E illustrates an example of an inductor having an elliptical cross-section.

FIG. 4F illustrates a rectangular cross-section of a multi-layer wire.

FIG. 7A shows an embodiment of a single turn inductor of the present invention having 1 layer.

FIG. 7B shows an embodiment of a single turn inductor of the present invention having 11 layers.

FIG. 7C illustrates an example of a single turn inductor of the present invention having 20 layers.

FIG. 7D illustrates an embodiment of a single turn inductor of the present invention having 26 layers.

FIG. 13 illustrates an embodiment of the multi layer multi turn inductor of the present invention comprising a cavity.

FIG. 14 shows an embodiment of the multi layer multi turn inductor of the present invention comprising four terminal connections.

FIG. 14A illustrates a magnified view of an embodiment of the terminal connections shown in FIG. 14.

DETAILED DESCRIPTION OF THE PREFERRED EMBODIMENTS

Figure 1:
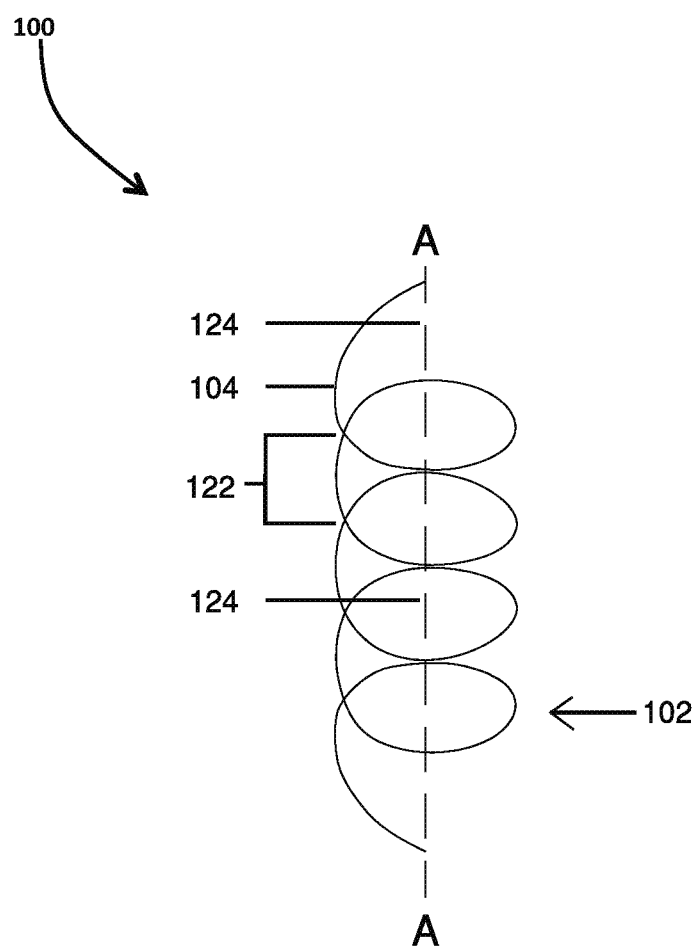
FIG. 1 illustrates an embodiment of a high-level diagram of an inductor structure.

In the following description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various technologies disclosed herein generally relate to methods, systems and apparatus to design, operate and manufacture an efficient multi-layer, multi-turn inductor of the present invention, and more specifically, to methods, systems and apparatus to design, operate and manufacture a multi-layer, multi-turn inductor for use in electrical circuits design to operate at radio frequencies (RF) of at least 3 kHz and greater.

An inductor is generally an electrical component or circuit that introduces inductance into a circuit. An inductor may consist of, but is not limited to, a wire or a set of wires. Inductance is generally a property of an electric circuit by which an electromotive force is induced as the result of a changing magnetic flux. The magnetic flux may change instantaneously or over time and thus become a time-varying magnetic flux. The magnetic flux is typically generated when a change in a frequency, a magnitude, a waveform shape, or combinations thereof, of the propagating electrical current occurs therewithin.

In addition, when the inductor is in motion, a motional electro motive force may develop. The motional EMF is dependent on the velocity of motion of the inductor or inductors and the magnitude of the electrical current flowing within the inductor. When the velocity of the inductor and/or the electrical current within the inductor increases, the resulting motional EMF also increases.

"Skin effect" is generally the tendency for an alternating current to concentrate near the outer part or "skin" of a conductor. For a steady unidirectional current through a homogeneous conductor, the current distribution is generally uniform over the cross section; that is, the current density is the same at all points in the cross section.

With an alternating current, the current is displaced more and more to the surface as the frequency increases. The conductor's effective cross section is therefore reduced so the resistance and energy dissipation are increased compared with the values for a uniformly distributed current. The effective resistance of a wire rises significantly with frequency; for example, for a copper wire of 1-mm (0.04-in.) diameter, the resistance at a frequency of 1 MHz is almost four times the dc value. "Skin depth" or "penetration depth" $\delta$ is frequently used in assessing the results of skin effect. It is generally accepted that the depth below the conductor surface at which the current density has decreased to about 1/e (approximately 37%) of its value at the surface. This concept applies strictly only to plane solids, but can be extended to other shapes provided the radius of curvature of the conductor surface is appreciably greater than $\delta$. For example, at a frequency of 60 Hz the penetration depth in copper is 8.5 mm (0.33 in.); at 10 GHz it is only $6.6 \times 10^{-7}$ m.

Wave-guide and resonant cavity internal surfaces for use at microwave frequencies are therefore frequently plated with a high-conductivity material, such as silver, to reduce the energy losses since nearly all the current is concentrated at the surface. Provided the plating material is thick compared to $\delta$, the conductor is as good as a solid conductor of the coating material. "Quality factor" is generally accepted as an index (figure of measure) that measures the efficiency of an apparatus like an inductor, a circuit, an antenna or a resonator. Via is defined herein as an electrically conductive connection from one layer to another.

A Litz wire is generally a wire constructed of individual film insulated wires bunched or braided together in a uniform pattern of twists and length of lay. Reference now is made in detail to the examples illustrated in the accompanying drawings and discussed below. FIG. 1 illustrates a high-level diagram of an inductor 100 for use in an electronic or electrical circuit. The inductor 100 comprises a coil 102 and a multi-layer wire 104. The shape of the coil 102 may be curved, circular, rectangular, triangular, trapezoidal, some other polygon, or conformal to fit within a constrained volume. FIG. 1 illustrates one exemplary configuration of the coil 102 in the form of a circular shaped coil 102. The configuration of the coil 102 may be curved, trapezoidal, solenoidal, spiral, spiral-solenoid, or the like. A solenoid coil follows a helical curve that may have multiple turns where each turn has the same radius. A spiral coil configuration may have a number of turns with a progressively increasing or decreasing radius. A spiral-solenoidal coil configuration is a combination of a spiral and solenoidal configuration. Other configurations known to those of ordinary skill may also be utilized to form the coil.

Figure 2A:
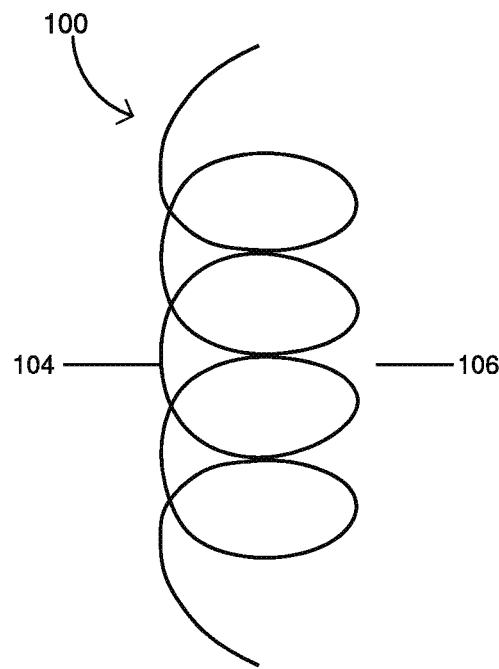
FIG. 2A illustrates an inductor in a circular solenoidal configuration.
Figure 2B:
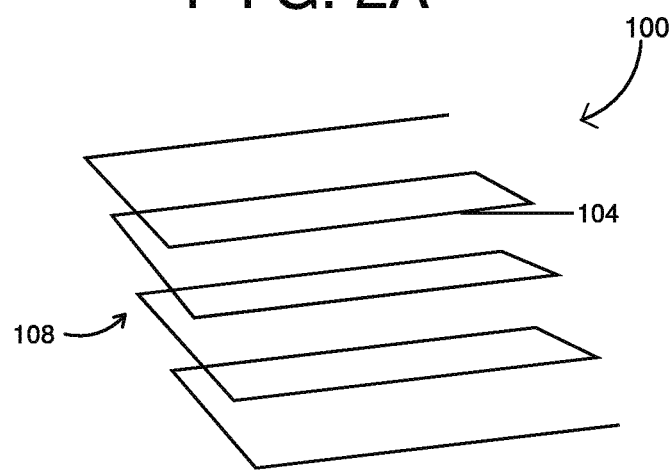
FIG. 2B illustrates an embodiment of an inductor in a square solenoidal configuration.
Figure 2C:
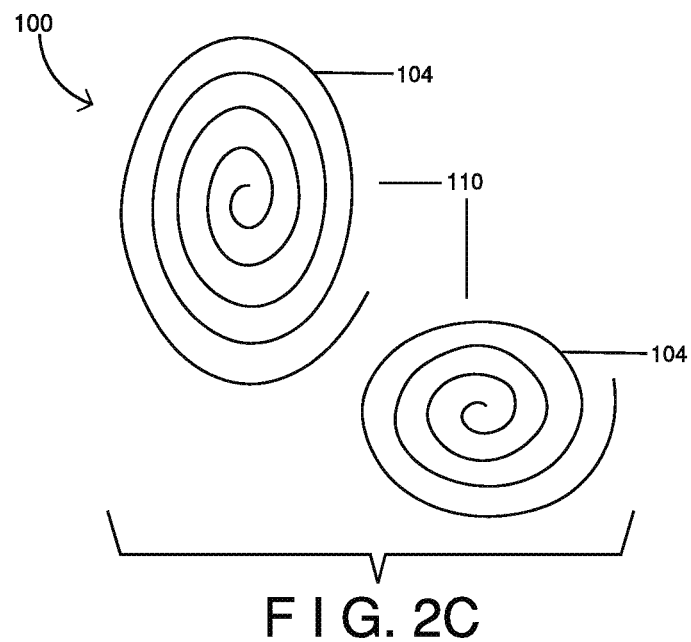
FIG. 2C illustrates an embodiment of an inductor in a circular spiral configuration.
Figure 2D:
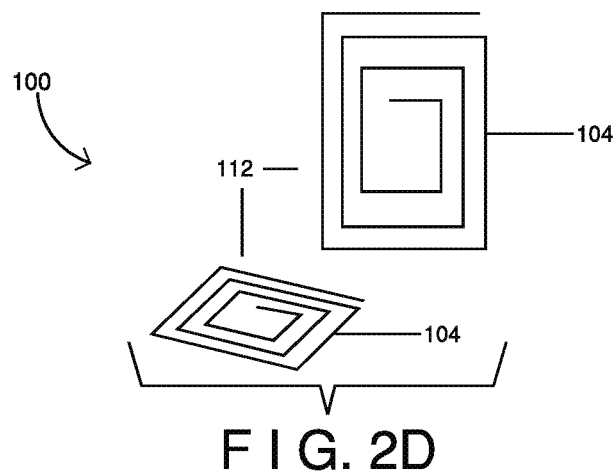
FIG. 2D illustrates an embodiment of an inductor in a square spiral configuration.

FIGS. 2A-2H illustrate examples of different inductor 100 configurations that may be utilized. FIG. 2A illustrates an embodiment of the inductor 100 in a circular solenoidal configuration 106. FIG. 2B illustrates an embodiment of the inductor 100 in a square solenoidal configuration 108. FIG. 2C illustrates an example of an inductor in a circular spiral configuration 110. FIG. 2D illustrates an example of an inductor in a square spiral configuration 112. It is understood that other spiral configurations, such as rectangular or triangular shape may also be utilized. FIG. 2E illustrates an example of the inductor 100 in a multi-layer square spiral configuration 114. It should be noted that although only two layers are illustrated in FIG. 2E, it is understood that any number of layers may be used. As will be described below, when multiple layers are used, the multiple layers may be connected using but not limited to vias, solder, tabs, wires, pins, or rivets. These connectors serve at least the following two purposes: (1) the connectors connect the layers of wire for the multi-layer wire 104; and (2) the connectors connect one turn of the multi-layer wire 104 to a second turn of the multi-layer wire 104. For example, a two-turn inductor 100 then, there would be at least one via from the first turn to the second turn. Other purposes may also be served by the connectors.

For each inductor 100, there exist an optimum number of connectors and an optimum location for each connector. Since there is no closed-form analytical solution for these, the optimal locations may best be obtained through iterative modeling. However, basic guidelines for optimizing are given herewithin:

It is preferred that there be at least 2 connectors connecting all of the layers that form a single conductor. These two connectors will ideally be at the two ends of the multi-layer wire (the input and the output of the multilayer wire)

It is preferred the total number of connectors should be chosen commensurate with the needs of a particular application. More than the optimum number of connectors will increase current paths which can lead to increased capacitance, increased resistance, reduced quality factor and higher bandwidth. It should also be noted that parasitic effects can become more pronounced when the overall length (height, depth) of the connector is greater than the optimum at a specific operating frequency. The length of the connector in essence is the height of the connector, and this should be kept smaller than about the (effective wavelength)/20, though keeping it within wavelength/10 could also lead to a workable embodiment, depending on the application. The reason for these restrictions is that the increased connector lengths will introduce significant phase differences between the different layers of the multilayer wire being used. These phase differences between the different layers will introduce unwanted capacitive effects, which will effectively lower self-resonance frequencies and increase losses.

Vias can be of the form commonly used in PCB technologies (for example, through-hole, buried, blind) or those utilized in semiconductor or MEMS technology. Alternatively, the via can be, but is not limited to, any conductive material that is laser-welded, welded, printed, soldered, brazed, sputtered deposited, wire-bonded and the like in order to electrically connect at least any two layers and/or all layers.

FIG. 2F illustrates an embodiment of an inductor 100 in a curved or circular spiral-solenoidal configuration 116. FIG. 2G illustrates an example of an inductor 100 in a square spiral-solenoidal configuration 118. FIG. 2H illustrates an example of an inductor 100 in a conformal solenoid configuration 120. The inductor 100 in a conformal configuration 120 may take the form of but is not limited to a circular or rectangular solenoid or a circular or rectangular spiral. Any of the inductor configurations (106, 108, 110, 112, 114, 116, 118 and 120) shown in FIGS. 2A-2H may be used with the present invention.

Figure 3A:
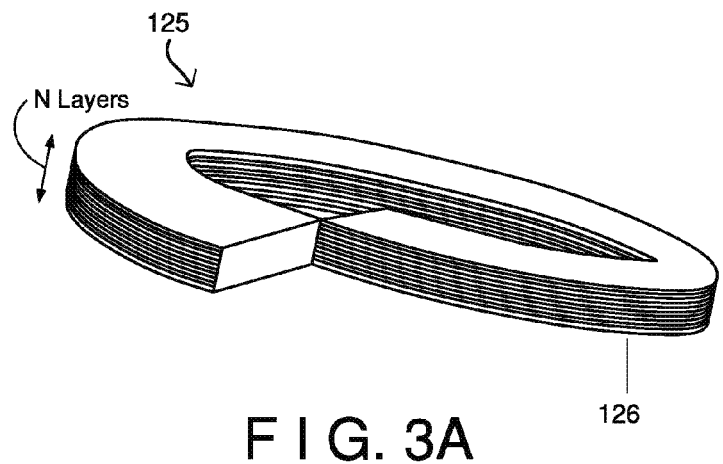
FIG. 3A shows an example of a single turn circular coil having N layers.
Figure 3B:
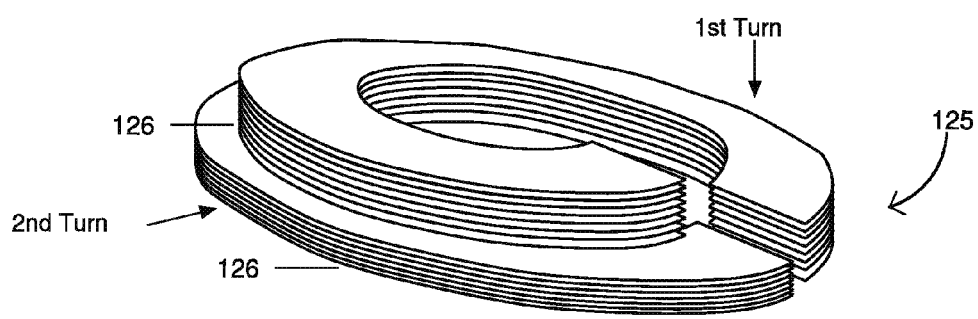
FIG. 3B illustrates an example of a double turn circular spiral-solenoidal coil were each turn has N layers and 2 times N total number of layers.

The coil 102 of FIG. 1 may have a plurality of turns 122. A turn 122 may be but is not limited to a bend, fold or an arc in the wire 104 until the wire 104 completes a revolution around a central axis A-A of the coil 102, more specifically a revolution around a central axis point 124. A turn 122 may be in the same or similar shape of the coil configuration, such as, for example, but not limited to a circle, a rectangle, a triangle, some other polygonal shape, or conformal to fit within a constrained volume. FIGS. 3A and 3B illustrate embodiments of a multi-layer multi-turn (MLMT) inductor 125 of the present invention. As shown, the MLMT inductor 125 comprises a single turn circular coil having N layers 126, where "N" is a number equal to or greater than one. FIG. 3B illustrates an additional embodiment of the MLMT inductor 125 comprising a double turn circular solenoidal configuration 106 coil of N layers 126.

In general, for any inductor 100, the inductance increases as $T^x$, while the resistance increases as $T^y$, where T is the number of turns 122. In ideal inductors, x and y are 2 and 1 respectively. There are other factors which affect the inductance and resistance (hence the quality factor) which calls for x and y to be less than 2 and 1 respectively. Referring to FIG. 10, three performance examples are given. The graph compares a 32 Layer-2 Turn inductor with a 32 Layer-1 Turn inductor and a 64 Layer-1 Turn inductor. The inductance and resistance for the 32 Layer-2 Turn inductor increase between 3-3.5 times and 1.7-3 times, respectively; over the 32 Layer-1 Turn inductor in the frequency range 1 MHz-200 MHz. This increase is very near expected values from simplistic analytical relations wherein resistance is approximately T; and inductance is approximately $T^2$.

Figure 4A:
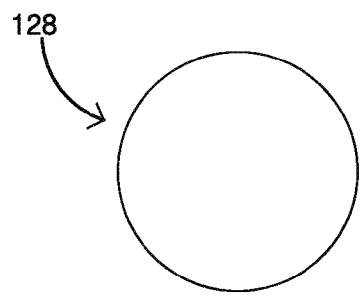
FIG. 4A illustrates an example of an inductor having a circular cross-section.
Figure 4B:
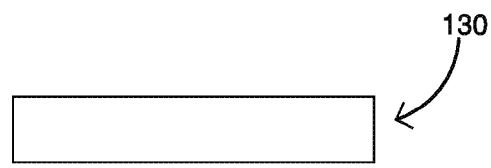
FIG. 4B illustrates an example of a conductor having a rectangular cross-section.
Figure 4C:
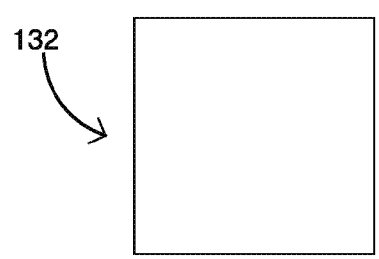
FIG. 4C illustrates an embodiment of an inductor having a square cross-section.
Figure 4D:
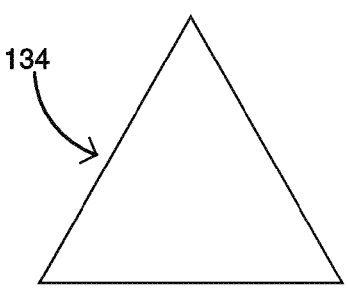
FIG. 4D illustrates an embodiment of an inductor having a triangular cross-section.

The multi-layer wire 104 in FIG. 1 may have but is not limited to a circular, rectangular, square, or triangular cross-sectional shape. In addition, other shapes known to those of ordinary skill may also be utilized. FIGS. 4A-4E illustrate examples of cross-sections of wires 104 that may be used in the design of an inductor. FIG. 4A illustrates an example of an inductor 128 having a circular cross-section. FIG. 4B illustrates an example of an inductor 130 having a rectangular cross-section 402. FIG. 4C illustrates an example of an inductor 132 having a square cross-section. FIG. 4D illustrates an example of an inductor 134 having a triangular cross-section. FIG. 4E illustrates an example of an inductor 136 having an elliptical cross-section. FIG. 4F illustrates a cross-sectional view of an embodiment of a multi-layer wire 104 having a first conductive layer 138 and a second conductive layer 140. An insulating material 430 separates the first conductive layer 138 from the second conductive layer 140. The first conductive layer 138 and the second conductive layer 140 are connected with vias 144 which traverse the insulating material 142. The conductive layers 138, 140 may comprise layers of conductive tape/ribbon/sheet/leaf or deposited metal having a metal thickness and metal strip width. Furthermore, conductive layers 138, 140 may comprise a liquid metal, a foamed metal or a conductive ink. The metal thickness of the first conductive layer 138 is identified by line B-B and the metal strip width of the first layer conductive 138 is identified by line C-C. In one example, the thickness of the conductive layer 138, 140 may be approximately twice a skin depth 146. The skin depth 146 may range from approximately one-half of the conductor depth to about equal to the conductor depth. Each layer in a turn will have substantially the same metal thickness and metal strip width.

Figure 5:
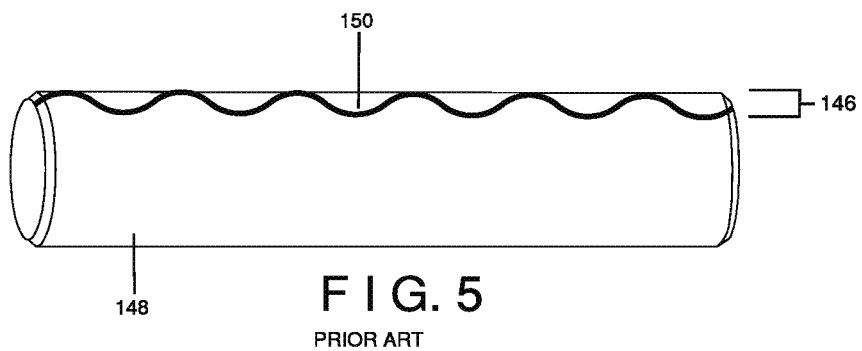
FIG. 5 shows an embodiment of approximate AC current distribution at increased frequency due to skin effect in a prior art wire.
Figure 5A:
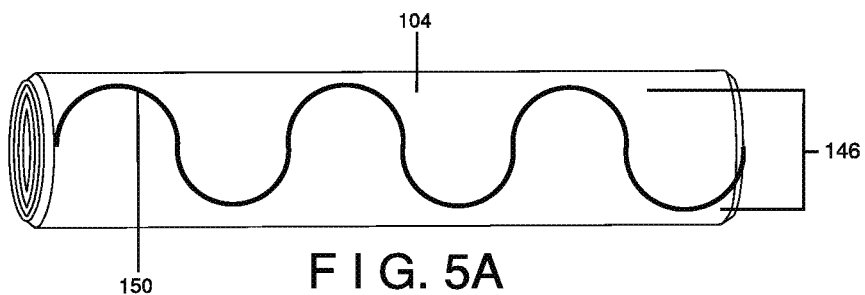
FIG. 5A illustrates an embodiment of AC current distribution through the multilayer wire of the present invention.
Figure 5B:
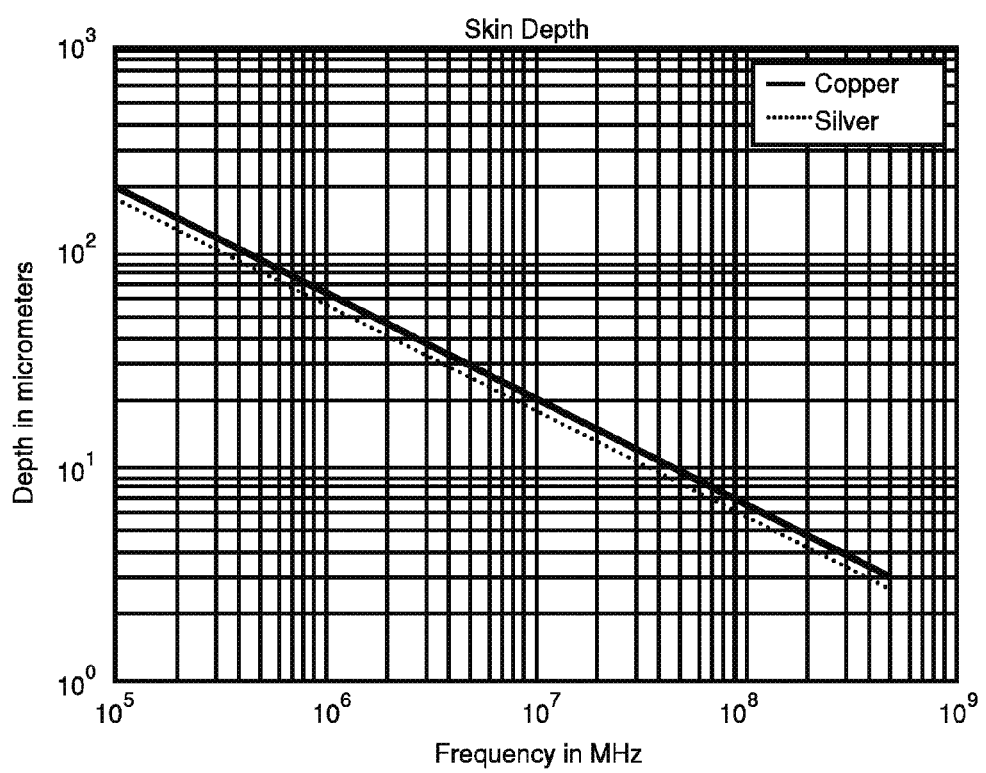
FIG. 5B shows a graph of skin depth versus frequency for a copper and silver wire of the prior art.

FIGS. 5 and 5A illustrate different embodiments of the skin depth 146. As illustrated in FIG. 5, a prior art metallic wire strand 148 is shown in which an electric current 150 is propagating therewithin. The electrical current 150 is shown propagating through the surface of the wire strand 148 of the prior art due to the skin effect as previously mentioned. The resulting skin depth 146 is shallow and resides near the exterior surface of the wire strand 148 of the prior art (FIG. 5). FIG. 5B is a graph of skin depth 146 as a function of frequency for standard wires 148 composed of copper and silver. As shown, skin depth decreases with increasing frequency for both copper and silver wires 148. In comparison, FIG. 5A illustrates electrical current 150 propagating through a multi layer wire 104 of the present invention. As shown, the structure of the multi-layered wire 104 of the present invention provides for a wider skin depth 146 that allows the electrical current 150 to propagate through a wider thickness of the multi layer wire 104, thereby increasing the efficiency of the propagation of the electrical current 150 therewithin.

The thickness of the insulating material may be sufficient to meet the needs of the application or equal to the minimum thickness possible by the available fabrication technology. In one embodiment where PCB technology is used for resonator manufacture, the minimum thickness as dictated by the core thickness and is about 150 microns. Current PCB technology allows core thickness as low as 25 microns. If semiconductor or MEMS fabrication is used, the thicknesses of both the conducting layers and the insulating layers can be as thin as a few 100 nanometers or even thinner. In a preferred embodiment, the dielectric layer thickness is less than 200 microns and as perfectly insulating as possible, and with a permittivity lower than 10.

Similarly, the dielectric layer 142 could be made from several materials, and can be of various configurations. For example, some applications may require extremely low parasitic capacitance. In such cases, a non-conducting dielectric with the lowest possible permittivity is preferred. Additionally, it may be desired to increase the insulating layer thickness to minimize the parasitic effects. Another example would be for applications that might require ferrite materials to increase inductance and/or increase magnetic shielding. In such cases, the dielectric layers may be replaced by a ferrite film/block or similar propertied configuration/material.

It will be apparent to one skilled in the art, therefore, that the insulating material 142 will be of a thickness such that the thickness is within the practical capabilities of the manufacturing technology used to manufacture the inductor 100 and compatible with the efficiency needs of the application for which the inductor is intended.

The material of the conductive layers 138, 140 may be copper or gold; however, other materials are possible. In addition, the material of the conductive layers 138, 140 may also comprise, a silver, a conductive polymer, a conductive adhesive, a conductive composite, or combinations thereof. To enhance conductivity, copper or gold with a layer of deposited silver may also be used. In the case where the inductor 100 is implanted and may be exposed to body fluids, then the typically known biocompatible materials should be utilized, including additions for enhancing conductivity. These may include, but are not limited to, conductive material taken from the group of: titanium, platinum and platinum/iridium alloys, tantalum, niobium, zirconium, hafnium, nitinol, cobalt-chromium-nickel alloys such as MP35N, Havar®, Elgiloy®, stainless steel, gold and its various alloys, palladium, carbon, or any other noble metal.

Depending on the application, the insulating material 142 may be (i) air, (ii) a polyimide material such as Kapton®, (iii) a dielectric with a low permittivity (such as, for example, Styrofoam®, silicon dioxide, or any suitable biocompatible ceramic), (iv) a non-conductive dielectric with a high permittivity, (v) a ferrite material, (vi) a pyroelectric material, or (vii) a combination of the materials listed above. The choice of material or combination of materials may result from factors such as the fabrication process, cost and technical requirements. For example, if a high capacitive effect is required to affect a lower self-resonance frequency of an inductor, a high permittivity dielectric might be preferred, or, a combination of materials including a ferrite film or ferrite block might be preferred to increase the self-inductance of the inductor. In addition, the use of a ferrite core may be used to provide increased performance.

Figure 6A:
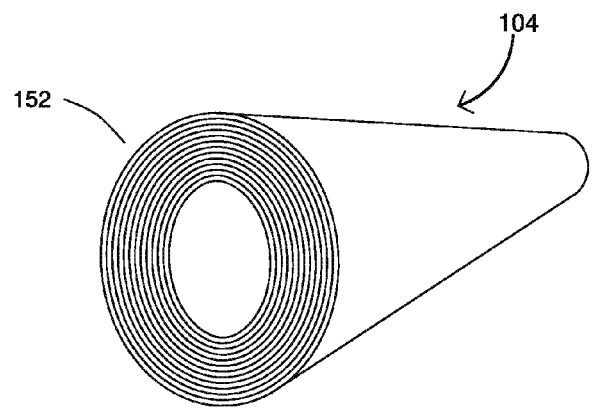
FIG. 6A illustrates an embodiment of a multi-layer wire of the present invention having a circular cross-section.
Figure 6B:
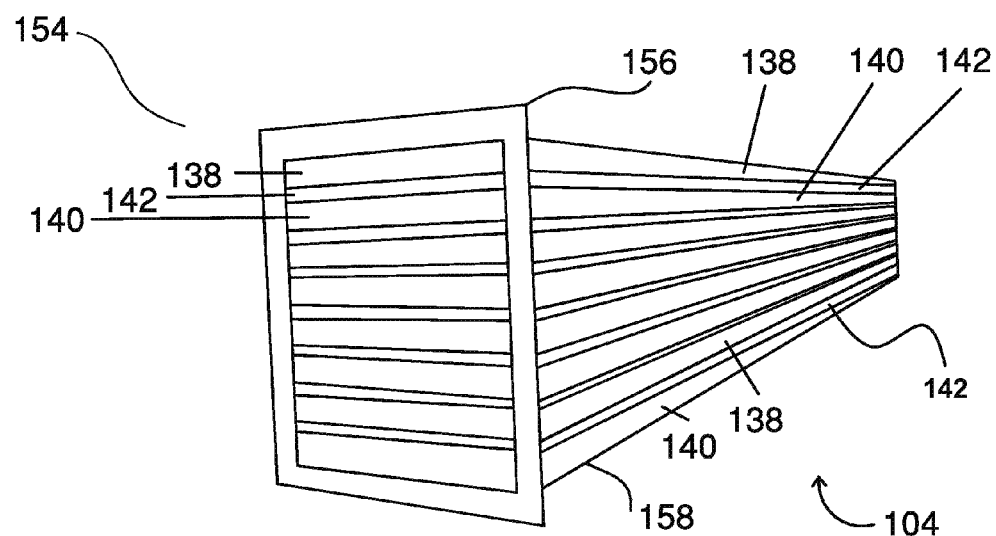
FIG. 6B illustrates an embodiment of a multi-layer wire of the present invention having a rectangular cross-section.
Figure 8:
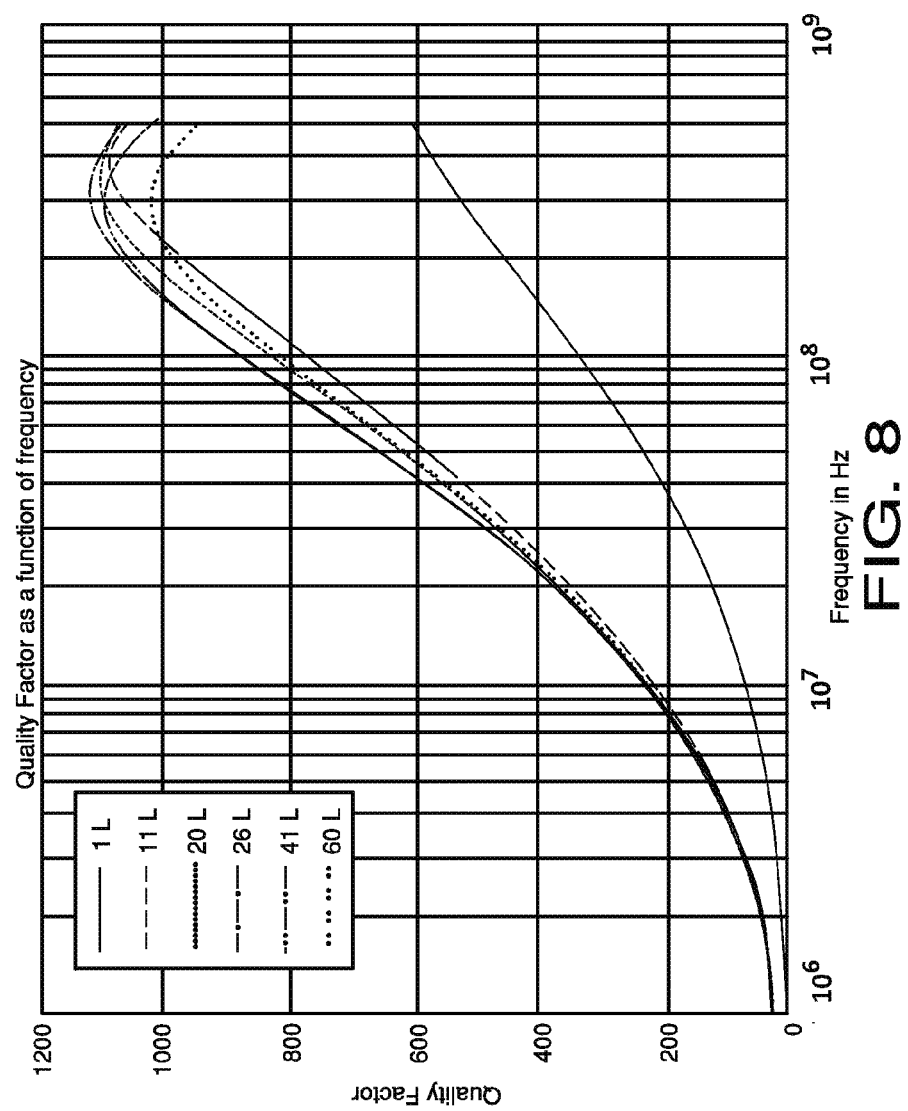
FIG. 8 shows a graph illustrating the value of the quality factor as a function of frequency for an embodiment of the inductor of the present invention.

FIGS. 6A and 6B illustrate embodiments of different cross-sectional configurations of the multi-layer wire 104. FIG. 6A illustrates a multi-layer wire 104 having a circular cross-section 152. FIG. 6B illustrates a multi-layer wire 104 having a rectangular cross-section 154. FIG. 6B illustrates a via 156 that connects the conductive layers 138, 140 that is positioned at a port or input 158, which is the beginning of the wire 104. Depending on the specific application, the positioning of the vias 144, 156 that connect the conductive layers 138, 140 may impact the performance of the inductor 100. For example, insufficient vias 144, 156 may lead to phase differences between the different layers 138, 140, 142. Conversely, an abundance of vias 144, 156 may lead to additional cyclical current paths that may increase the resistive loss. The vias 144, 156 may be located at the beginning of the wire (e.g., port, input, etc), or at one or more locations along the wire. Additionally, the vias 144, 156 between one set of two or more conductive layers 138, 140 may be at a different location than another set of two or more conductive layers 138, 140. It is understood that several variations may be possible depending on the application and the system design. The via 144, 156 can be made using techniques standard to the technology being utilized for the fabrication of the multi-layer multi-turn structure. In other cases, the vias 144, 156 can be implemented using soldering techniques, such as, by connecting the several layers 138, 140 at via locations using electric solder, welded tabs, laser weld tacking, or other commonly known electrical connecting techniques.

The MLMT inductor 125 of the present invention may also be designed to achieve a specified inductance and performance efficiency performance in a configuration that is restricted in size. More specifically, a size that is restricted dimensionally in length, width, height or any combination thereof, or a size that is restricted by volume, or both dimension(s) and volume. To achieve a specific inductance having a lower electrical resistance in having a smaller size, multiple conductive layers 138, 140 are utilized that are preferably connected in parallel. Furthermore, parallel electrical connections between conducting layers 138, 140 is preferred in achieving higher inductance values in the MLMT inductor structure 125.

In addition, a thin layer of a conductive material, i.e., a conductive trace, may be deposited the surface of an insulative layer and/or conductive layer.

When designing for combinations of lower resistance and higher inductance, one embodiment is to construct the MLMT inductor 125 comprising at least two conductor layers 138, 140 that are electrically connected in parallel. In another embodiment, multiple subassemblies comprising alternate conductive 138, 140 and insulative layers 142 may be electrically connected in series. For example, a first inductor subassembly comprising a first conductor layer spaced apart from a second conductor layer, a first insulator layer positioned in the space between the first and second conductor layers wherein the first and second conductor layers are electrically connected in parallel may be electrically connected in series to a second inductor subassembly comprising a third conductor layer spaced apart from a fourth conductor layer, a second insulator layer positioned between the third and fourth conductor layers, wherein the third and fourth conductor layers are electrically connected in parallel. Furthermore, the first, second, third or fourth conductive layers may comprise a thin conductive layer, or conductive trace, of the order of microns, composed of a similar or differing conductive material. Likewise the first and second insulative layers may comprise a thin insulative layer or insulative trace, of the order of microns.

Furthermore, this embodiment may be constructed having respective conductor and insulative layers 138, 142 with layer thicknesses that are the same or different from each other. Likewise, the respective conductive and insulative layers 138, 142 may be constructed with a width that is the same or different.

Further, for all the wires or traces discussed above, the width, the diameter, or dimensions of the shape of the wire or conductive trace may differ or be the same. In each case, the proximity effect must be considered in achieving the final performance. It will be obvious to those skilled in the art that any of the elements given in the embodiments above may be used to achieve a specific inductance and/or particular design specification requirements. As defined herein, "proximity effect" is defined as the obstruction of the flow of electrical current that caused is caused by the magnetic field(s) of adjacent conductor(s). The alternating magnetic field emanating from adjacent conductors induces eddy currents in adjacent conductors, thus altering and obstructing the overall distribution of current flowing through them.

As will be described herein, the inductor 125 is preferably designed with a high inductor quality factor (QF) to achieve efficient transfer of inductance that reduces intrinsic resistive losses of the inductor at high frequencies. The quality factor is the ratio of energy stored by a device to the energy lost by the device. Thus, the QF of an inductor is the rate of energy loss relative to the stored energy of the inductor.

A source device carrying a time-varying current, such as an inductor, possesses energy which may be divided into three components: 1) resistive energy ($W_{res}$), 2) radiative energy ($W_{rad}$), and 3) reactive energy ($W_{rea}$). In the case of inductors, energy stored is reactive energy and energy lost is resistive and radiative energies, wherein the inductor quality factor is represented by the equation $Q=W_{rea}/(W_{res}+W_{rad})$.

In operation, radiative and resistive energies, in the form of radiative and resistive electrical resistances, are released by the device, in this case the inductor, to the surrounding environment.

As such, inductors 125 of the present invention are designed to minimize both resistive and radiative energies while maximizing reactive energy. In other words, inductors, particularly inductors 125 operating at RF frequencies and greater, benefit from maximizing Q. In general, this is accomplished through a reduction in the "skin effect" of the conducting materials within the inductor. The "skin effect" is generally reduced through the utilization of combining a multitude of conductors having a thin thickness or narrow diameter thereby increasing the overall cross-sectional area of the conducting skin within the inductor.

By example, the quality factor of an inductor varies according to the following relationship:

$$Q = \frac{2\pi f L}{R}$$

where f is the frequency of operation, L is the inductance, and R is the total resistance (ohmic+radiative). As QF is inversely proportional to the resistance, a higher resistance translates into a lower quality factor.

A higher quality factor may be achieved using multiple layers in a multi-layer wire 104 for a single turn of coil. Increasing the number of turns 122 in a coil 102 may also be used to increase the quality factor of the structure. For a design at a constant frequency, there may be an optimum number of layers 126 to reach a maximum quality factor. Once this maxima is reached, the quality factor may decrease as more layers are added. The design variables that may be used for the multi-layer multi-turn inductor 125 structure include:

a. Metal strip width, $w_n$ (e.g. $w_1$: width of the $1^{st}$ conductive layer, $w_k$: width of the $k^{th}$ conductive layer). Also referred to as metal width or strip width
b. Number of conductive layers 138, 140 per turn, $N_n$ (e.g. number of layers in $1^{st}$ turn, $N_1$)
c. Thickness of each conductive layer 138, 140, $d_n$ (e.g. $d_1$: thickness of $1^{st}$ layer, $d_k$: thickness of $k^{th}$ layer)
d. Thickness of insulation, $di_n$ (e.g. $di_1$: thickness of insulation under $1^{st}$ layer, $di_k$: thickness of insulation under $k^{th}$ layer)
e. Number of turns 122, T
f. Number of vias 144, 156 connecting the different conductive layers 138, 140 in each turn
g. Location of vias 144, 156 connecting the different conductive layers 138, 140 in each turn
h. Shape (circular, rectangular, some polygon; depends on the application; for e.g. could be conformal to fit just outside or just inside some device or component)
i. Configuration: solenoidal, spiral, spiral-solenoidal, etc)
j. Dimensions (length, width, inner radius, outer radius, diagonal, etc.)

The quality factor (Q) of the inductor 125 can also be defined as (frequency (Hz) X inductance (H))/resistance (ohms), where frequency is the operational frequency of the circuit, inductance is the inductance output of the inductor and resistance is the combination of the radiative and reactive resistances that are internal to the inductor.

Below, exemplary multi-layer multi-turn designs based on the above parameters will be described. In one example, the inductor 125 may be a single turn circular coil having multi-layer wire 104, as illustrated in FIGS. 7A-7D. The single turn coil includes a single turn and may include a metal strip width of approximately 1.75 mm, a metal thickness of approximately 0.03 mm, an insulating layer of approximately 0.015 mm, and an outer radius of approximately 5 mm. The wire 104 may have between 5 and 60 layers 126, such as 5, 11, 20, 26, 41, or 60 layers 126. For example, FIG. 7A shows a single turn inductor having 1 layer 126, FIG. 7B shows a single turn inductor having 11 layers 126, FIG. 7C shows a single turn inductor 125 having 20 layers 126, and FIG. 7D shows a single turn inductor having 26 layers. Although specific examples are shown in FIGS. 7A-7D, it is understood that the wire 104 may have less than 5 or more than 60 layers 126 in order to achieve a high quality factor. The corresponding coil thickness for the range of 5 to 60 layers 126 may be between approximately 0.2 mm to 3 mm, such as for example, 0.2, 0.5, 1, 1.25, 2.05, or 3 mm, respectively. As mentioned above, it is understood that by varying the number of layers 126 in the wire 104, the number of turns 122, the metal thickness, and the metal strip width, a higher quality factor may be obtained. For example, for a 1 layer single turn coil 102 having a metal thickness of 0.03 mm and a metal strip width of 1.75 mm, the quality factor at 10 MHz is approximately 80. Increasing the number of layers 126 from 1 to 11 and keeping a metal thickness of 0.03 mm and a metal strip width of 1.75 mm, the quality factor is increased to approximately 210. Generally, an increase in the number of layers 126 per turn results in an increase in quality factor until maxima is reached, after which the quality factor starts to decrease. This decrease may occur when the total height of the inductor becomes comparable to its radius. With electrical components, the degradation starts due to greatly increased parasitic effects due to the multiple layers (e.g. capacitance and proximity effects). In the present example, increasing the layers 126 to 20, 26, 41 and 60 results in quality factors of approximately 212, 220, 218 and 188, respectively.

Two inductor configurations were considered, the specifics of which are provided in Tables 1 and 2 below. The results indicate that the present teachings allow for inductors comprising significantly higher quality factors than currently existing inductors utilizing prior art technology. The performance improvement shown herein applies when other known methods of construction are utilized.

EXAMPLES

Table 1 illustrates an example wherein a TDK model MLG1608B4N7ST inductor was compared to a computer generated model of an MLMT inductor 125 of the present invention. The MLMT inductor 125 modeled such that it provides an inductance that is similar to the TDK model inductor. As shown in Table 1 below, the MLMT inductor of the present invention has a similar inductance of about 4.72 nH vs. the 4.7 nH of the TDK inductor operating at 100 MHz. However, the quality factor of the MLMT inductor 125 was determined to be about 2.8 times greater than the TDK inductor operating at about 100 MHz.

TABLE 1

| | TDK | | MLMT Inductor | |
|---|---|---|---|---|
| Frequency | Inductance (nH) | Quality Factor | Inductance (nH) | Quality Factor |
| 100 MHz | 4.7 | 10 | 4.72 | 38 |

Table 2 illustrates an example wherein a Sunlord model HQ1005C1N5 inductor was compared to a computer generated model of an MLMT inductor 125 of the present invention. The MLMT inductor 125 was modeled to provide an inductance that is similar to the Sunlord model inductor. As shown in Table 2 below, the MLMT inductor 125 of the present invention has a similar inductance of about 1.7 nH vs. the 1.5 nH of the TDK inductor operating at 250 MHz. However, the quality factor of the MLMT inductor was determined to be about 1.25 times greater than the Sunlord inductor operating at about 250 MHz.

TABLE 2

| | Sunlord | | MLMT Inductor | |
|---|---|---|---|---|
| Frequency | Inductance (nH) | Quality Factor | Inductance (nH) | Quality Factor |
| 250 MHz | 1.5 | 20 | 1.7 | 45 |

Figure 9B:
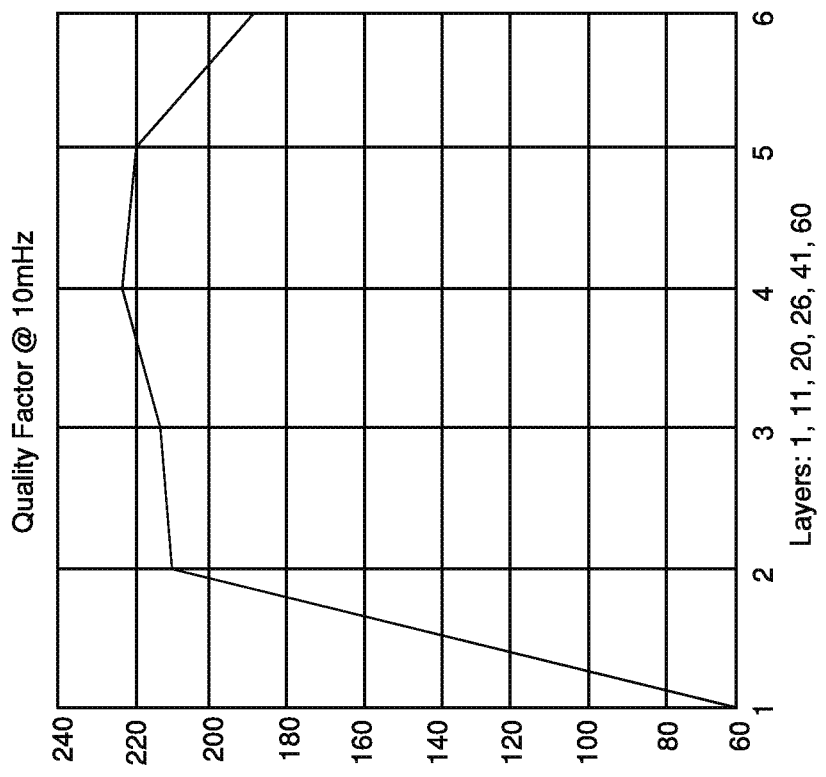
FIG. 9B is a graph illustrating the resultant quality factor at 10 MHz for the given number of layers.
Figure 9A:
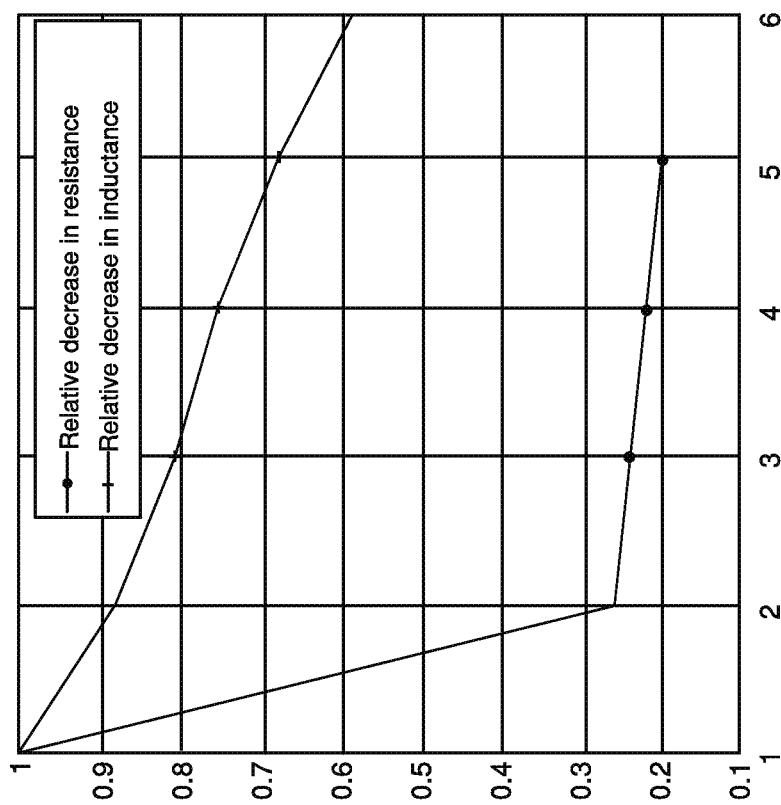
FIG. 9A is a graph illustrating the relative changes in resistance and inductance with the number of layers.

It is also understood that the metal strip width may be increased to achieve a higher quality factor. FIGS. 8, 10A, 11A, 12A, 12B, and 12C provide graphs of the value of the quality factor as a function of frequency. FIG. 9A is a graph illustrating the relative changes in resistance and inductance with the number of layers. FIG. 9B illustrates the resultant quality factor at 10 MHz. It should be noted that with regard to FIGS. 9A and 9B, the data points on the graph correspond as data point 1 is for 1 layer, data point 2 is for 11 layers, data point 3 is for 20 layers, data point 4 is for 26 layers, data point 5 is for 41 layers, and data point 6 is for 60 layers. To ensure electrical flow through all layers of the structure, it is preferable that at least two vias 144, 156 be included for any multi-layer wire 104 and/or structure. These two vias 144, 156 are preferably located at the ports 158 of the wire/structure 104. As can be seen from FIGS. 8 and 9A-9B, optimal performance for 10 MHz is achieved for an inductor 125 configuration having 26 layers 126 and 1 turn 122. For this inductor configuration, the peak quality factor is obtained around 35 MHz and is approximately 1100.

In another example, the inductor 125 may be a single turn circular coil of multi-layer wire 104 and may have a metal strip width of approximately 1 mm, a metal thickness of approximately 0.01 mm, an insulating layer of approximately 0.005 mm, and an outer radius of approximately 5 mm. The wire 104 may have between 16 and 128 layers, such as 16, 32, 64, or 128 layers. However it is understood that the wire 104 may have less than 16 or more than 128 layers 126 in order to achieve a high quality factor. The corresponding coil thickness for the range of 16 to 128 layers 126 may be between approximately 0.25 mm to 2 mm, such as for example, 0.25, 0.5, 1, or 2 mm, respectively. In this example, the quality factor improves with increasing the number of layers, with larger quality factors achieved at higher frequencies. For example, at a frequency of 10 MHz, the quality factor for 16, 32, 64 and 128 layers is approximately 127, 135, 140 and 185, respectively. The peak quality factor increases to nearly 2900 at approximately 450 MHz under these design parameters.

The relative resistance may be lowest around the frequency at which the conductor thickness is about twice the skin depth. In this example, that frequency is 160 MHz.

Figure 10A:
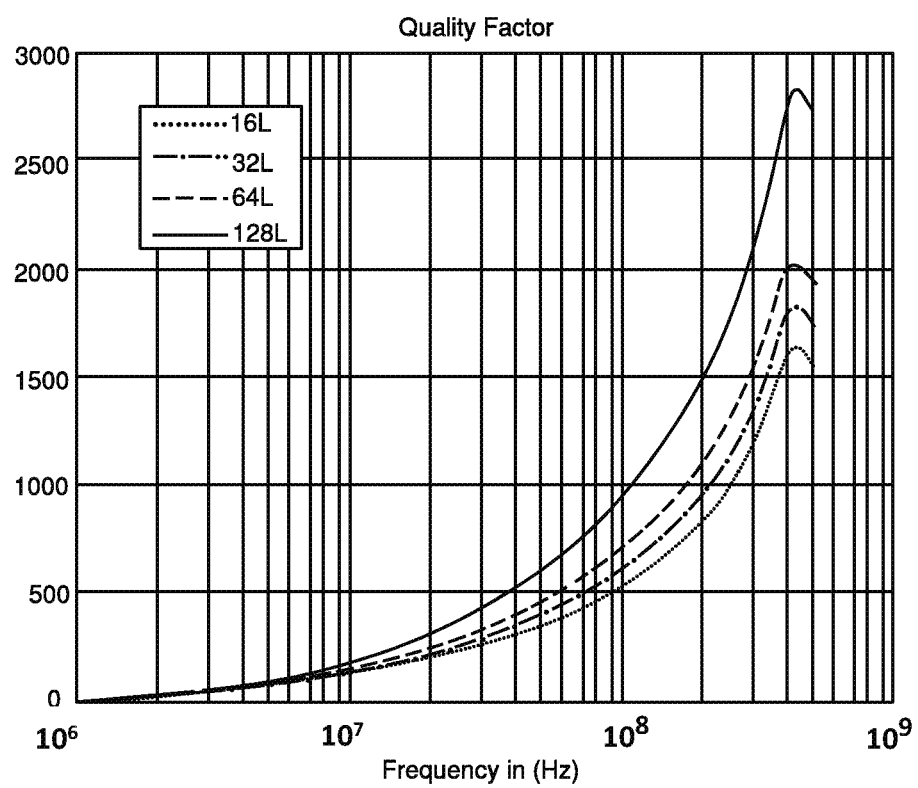
FIG. 10A is a graph illustrating the quality factor as a function of frequency.
Figure 10B:
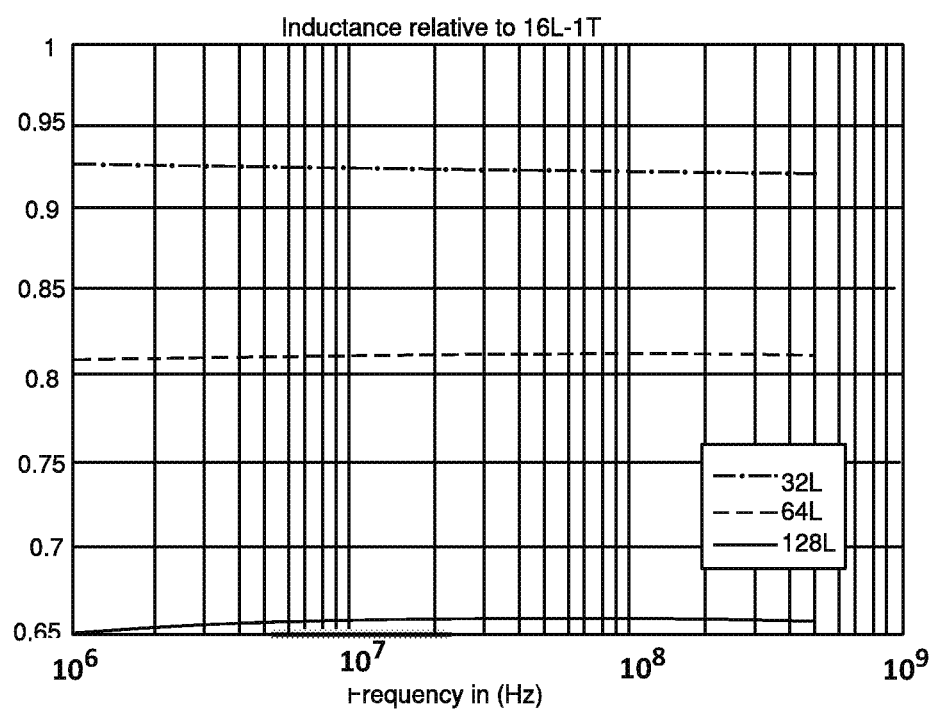
FIG. 10B is a graph illustrating the inductance relative to a 16 layer coil as a function of frequency.
Figure 10C:
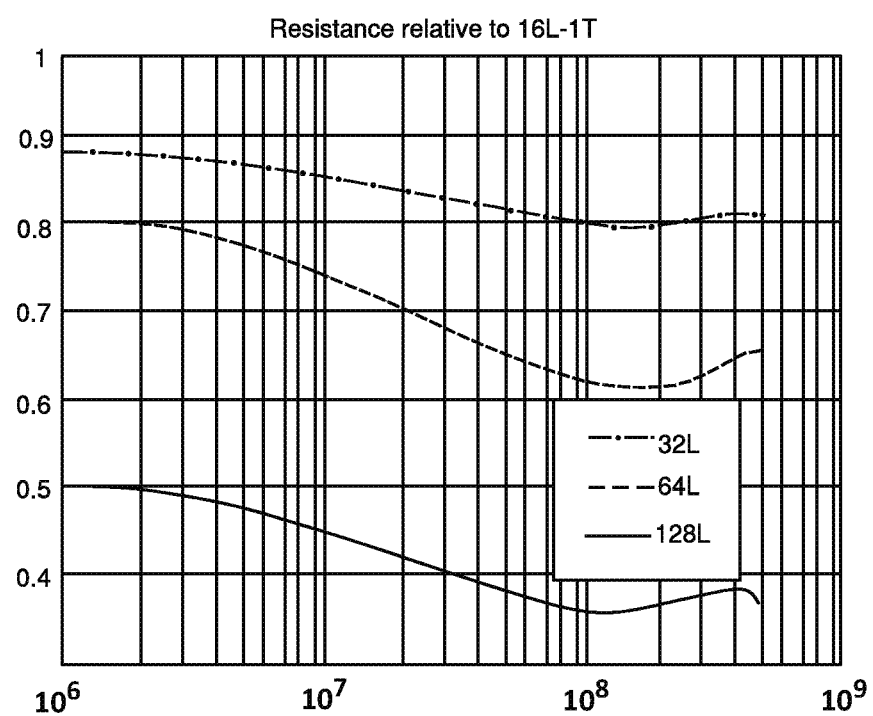
FIG. 10C shows a graph illustrating the resistance relative to the 16 layer coil as a function of frequency.

FIGS. 10A-10C are graphs illustrating the performance parameters and trends. FIG. 10A is a graph illustrating the quality factor as a function of frequency. FIG. 10B is a graph illustrating the inductance relative to a 16 layer coil as a function of frequency. FIG. 10C is a graph illustrating the resistance relative to the 16 layer coil as a function of frequency. As can be seen in FIG. 10A, the quality factor improves with an increasing number of layers with relatively larger quality factors at higher frequencies. This is further shown in FIGS. 10B and 10C where it is shown that where the inductance is relatively constant (as compared to a 16 layer 1 turn coil) with frequency, while the resistance decreases as frequency increases as shown by the troughs around 100 MHz in FIG. 10C. The peak quality factor goes up to approximately 2900 at around 450 MHz.

Figure 11A:
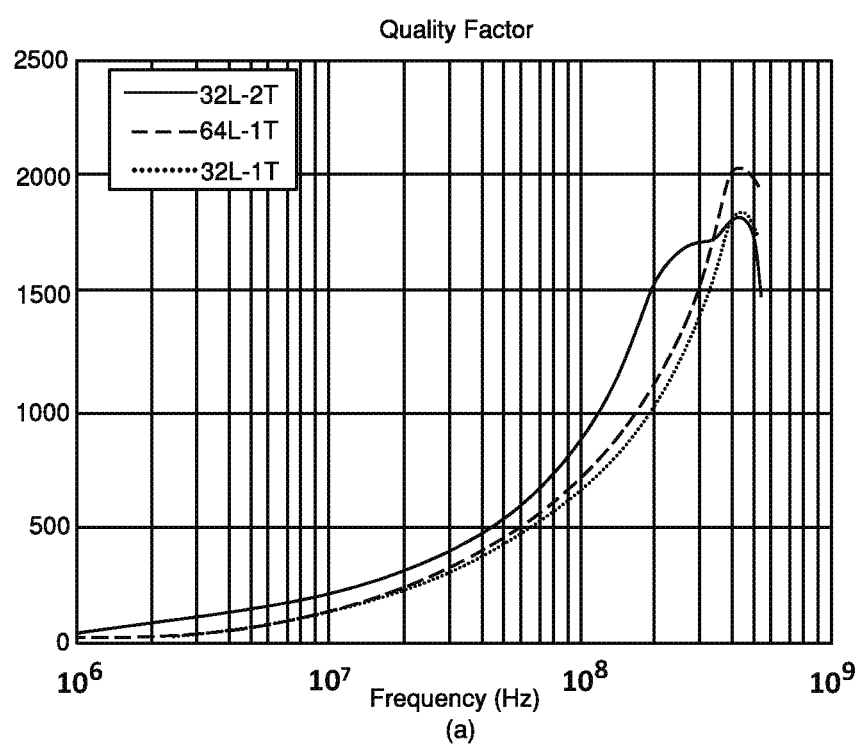
FIG. 11A shows a graph illustrating the quality factor as a function of frequency.
Figure 11B:
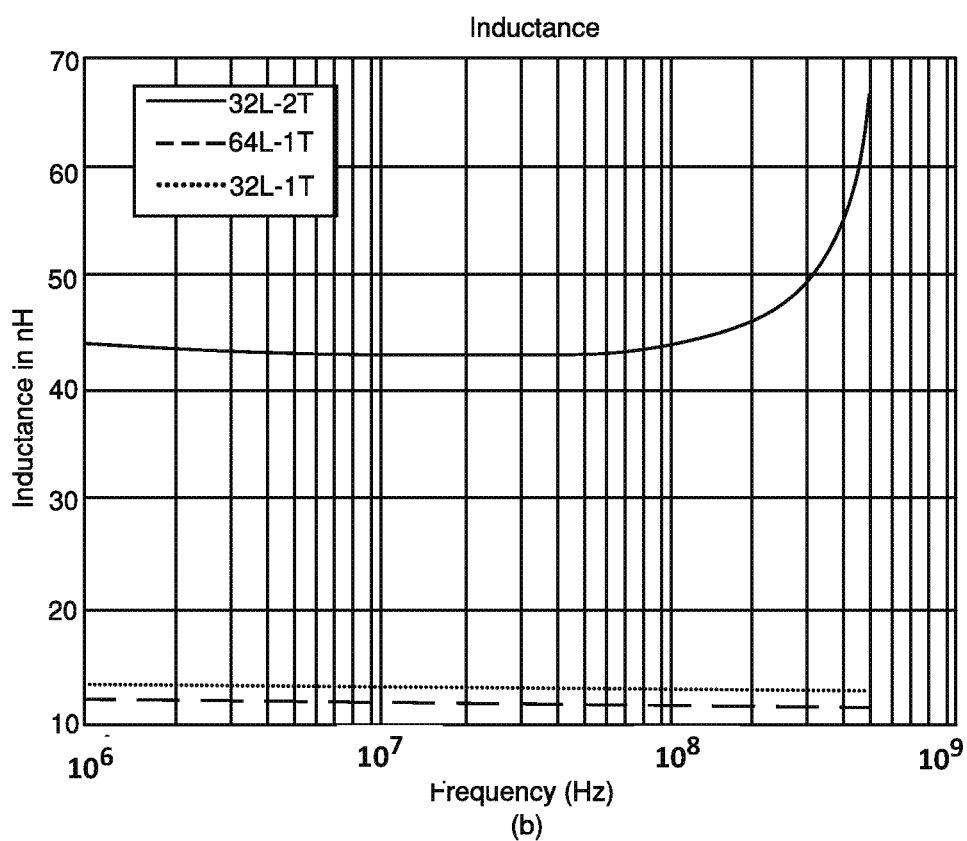
FIG. 11B is a graph illustrating the inductance as a function of frequency.
Figure 11C:
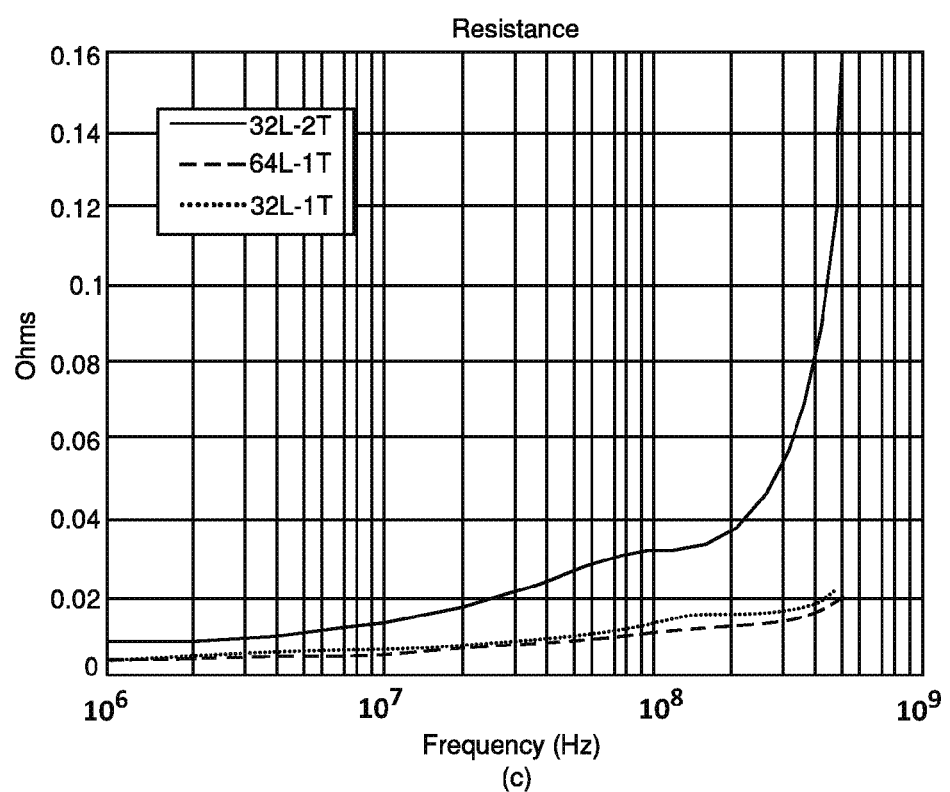
FIG. 11C is a graph illustrating the resistance as a function of frequency.

In yet another example, all design parameters are the same as in the preceding example for a 32 layer wire 104, except the number of turns is doubled, resulting in a double turn circular coil. The inductance and resistance for this 32 layer, double turn inductor 125 increase between 3 to 3.5 times and 1.7 to 3 times, respectively, over the 32 layer, single turn inductor in the frequency range of 1 MHz to 200 MHz. FIGS. 11A-C are graphs illustrating the performance parameters and trends for the 32 layer, double turn inductor 125 compared to the 32 and 64 layer, single turn inductors 125 in the preceding example. FIG. 11A is a graph illustrating the quality factor as a function of frequency. FIG. 11B is a graph illustrating the inductance as a function of frequency. FIG. 11C is a graph illustrating the resistance as a function of frequency. As can be seen in FIGS. 11A-C, for the 32 layer, double turn inductor 125 at frequencies below about 200 MHz, the inductance is nearly constant and the resistance follows trends similar to the single turn embodiments. At frequencies greater than 200 MHz, both the inductance and resistance rise rapidly due to the contribution of parasitic capacitance, which is explained below. Even though the quality factor remains high at frequencies greater than 200 MHz, there may be significant electric fields present due to the capacitive effect, which may not be acceptable in some applications.

Figure 12A:
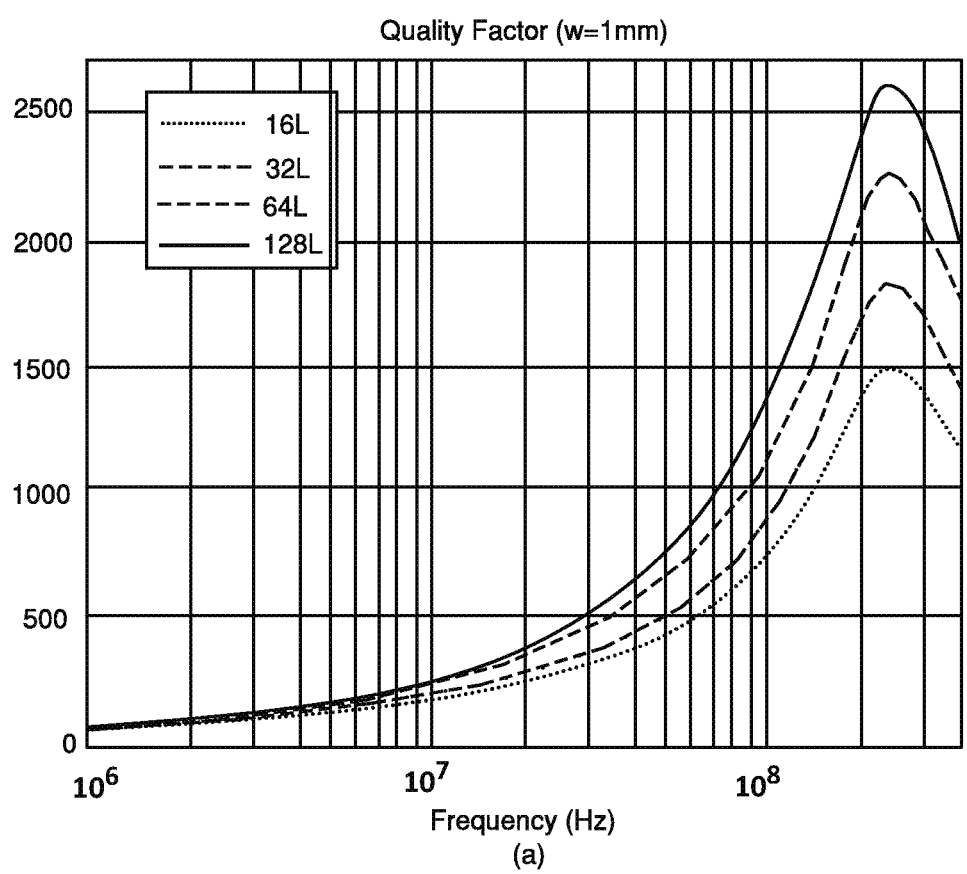
FIG. 12A is a graph illustrating the quality factor as a function of frequency for a coil having a metal strip width of 1 mm.
Figure 12B:
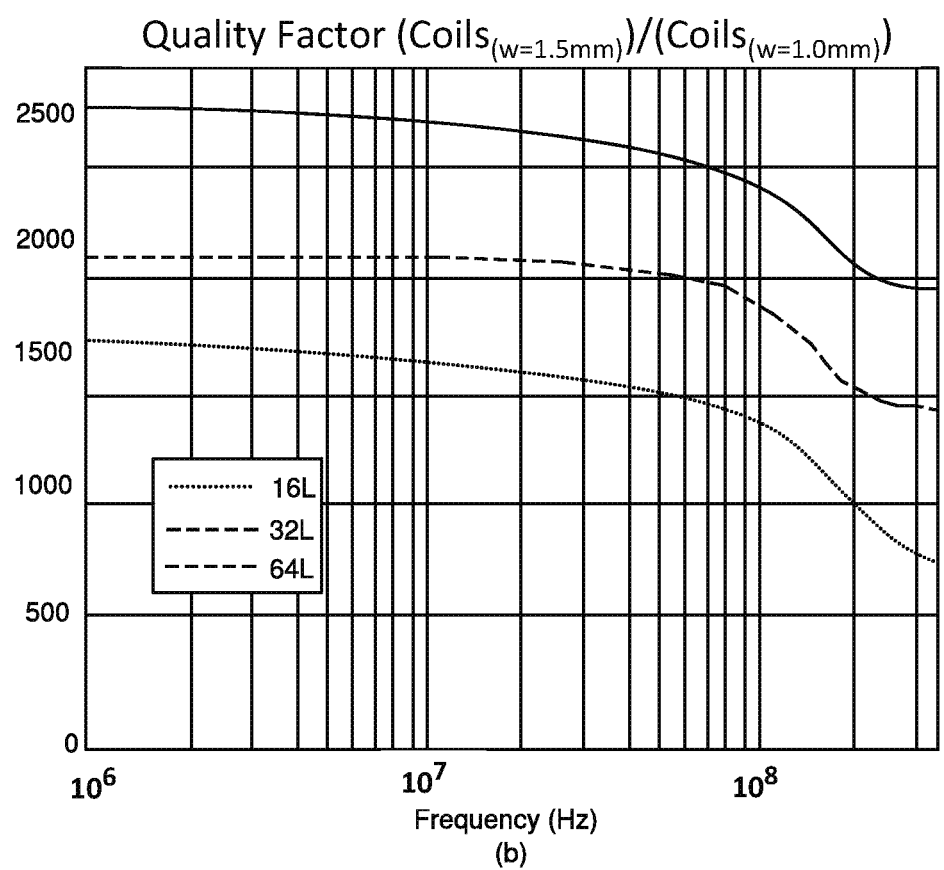
FIG. 12B is a graph illustrating the relative increase in quality factor for a coil having a metal width of 1.5 mm.
Figure 12C:
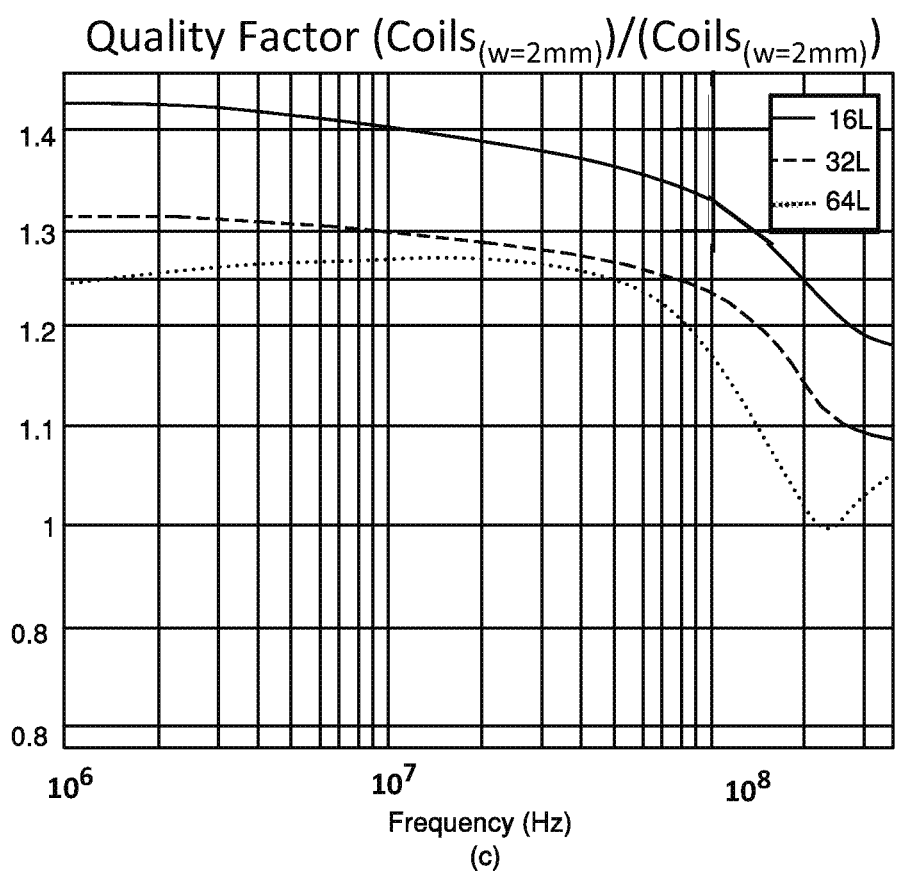
FIG. 12C is a graph illustrating the relative increase in quality factor for a coil having a metal width of 2 mm.

It is also contemplated that other designs may be used for the inductor in order to achieve higher quality factors. For example, for a single turn circular coil of multi-layer wire 104 that may have between 16 and 128 layers, such as 16, 32, 64, or 128 layers, the coil may include a metal strip width of approximately 1 mm, a metal thickness of approximately 0.01 mm, an insulating layer 142 of approximately 0.01 mm, and an outer radius of approximately 10 mm. Increasing the width of the metal reduces the resistance and the inductance, resulting in a higher quality factor. Due to the overall large size of the inductor (outer radius ~10 mm), the relatively small increase in the width (w) does not reduce the inductance. It should be noted that the same increase in metal width for a smaller inductor, such as, for example, with outer radius approximately 5 mm, the decrease in inductance would have been higher. FIGS. 12A-C are graphs illustrating the quality factors as a function of frequency for this example with a metal strip width of approximately 1 mm, 1.5 mm and 2 mm, respectively. In this example, the quality factor at 379 MHz is approximately 1425 for a metal strip width of 1 mm. Increasing the metal strip width to 1.5 mm and 2 mm increases the quality factor to approximately 1560 and 1486, respectively.

It should be noted that all the QF values mentioned above for the inductors are in free space (conductivity=0, relative permittivity=1). It is expected that the presence of a real world environment will affect the QF. For example, an inductor with a QF ~400 in free space could have the QF decrease when it is placed next to the human body. Further, if the inductor is placed inside the human body with little or no insulating coating, the QF might further decrease. Applying a coating sufficiently thick or enclosing in a sufficiently large package before placing inside the human body might decrease the change in the QF of the inductor. It is expected that similar changes in QF characteristics will occur in any medium and in the proximity of any material, with the deviation from free space depending on the electrical properties of the material/medium and the distance from it. Such a decrease in the quality factor of inductors, particularly those inductors of the prior art, may compromise the performance of the electrical circuit of and/or associated device within which the inductor operates. Since the quality factor of prior art inductors is generally less than the multi-layer, multi-turn inductor 125 of the present invention, a further reduction in the quality factor may result in dysfunction of the circuit or the inoperability of the device within which the inductor resides.

In yet another preferred embodiment as shown in FIG. 13, the MLMT inductor 125 of the present invention may comprise a cavity 160 that resides within the perimeter of the MLMT structure. While inductors are commonly fabricated with an air-core, the inductors fabricated using multilayer technologies such as thin film, ceramic and other similar processes (e.g. rigid printed circuit board (PCB), flexible printed circuit board (flex PCB), low temperature cofired ceramic (LTCC), high temperature cofired ceramic (HTCC), etc.) have the conductive turns mostly immersed in the substrate material. In certain instances, this substrate material may affect the performance parameters of the inductor. For example, it may lower the QF as well as the self-resonance frequency. This effect becomes more dominant with increasing frequency as it stems from the interaction of the electric and magnetic fields with the substrate material. It is also more dominant in substrate materials with a high dielectric constant. A way to reduce the substrate effect may be to introduce a cavity within the inductor volume (this may not be possible in all inductor configurations and/or fabrication processes). This cavity may be introduced during the fabrication process, or may be created during a post-processing step.

The cavity 160 preferably extends vertically through the structure of the inductor such that it extends through the top and bottom surfaces of the MLMT inductor 125 structure. As shown, the cavity 160 comprises a cavity width 162 and a cavity length 164 and a cavity depth 166 that defines a cavity sidewall 168. In the embodiment shown in FIG. 13, the cavity width 166 is about equal to the width of the inductor 125, the cavity length 164 is about equal to the length of the inductor 125 and the cavity depth 166 is about equal to the depth of the inductor 125. Alternately, the cavity width 162 may range from about 50 percent to about 99 percent of the width of the inductor 125. The cavity length 164 may range from about 80 percent to about 99 percent of the length of the inductor 125. Preferably, the cavity depth 166 may be about equal to the depth of the inductor 125 such that the cavity 160 extends through the top and bottom surfaces of the inductor 125 of the present invention.

The cavity 160 feature within the inductor structure is designed to further improve the quality factor of the inductor 125 at a given operating frequency or frequencies as compared to an inductor without the cavity 160 feature. In general, the incorporation of the cavity 160 feature reduces the degrading effects of parasitic capacitance ($C_{par}$) and parasitic resistance ($R_{par}$). Parasitic capacitance is herein defined as undesirable capacitance that exits internally within the structure of a circuit element. Parasitic capacitance causes the behavior of the circuit element to divert from its intended behavior. Parasitic resistance is herein defined as undesirable electrical resistance that manifests itself within an electrical circuit or component, such as a capacitor or inductor.

As previously mentioned, the quality factor of an inductor can generally be defined as $$\frac{X_{\mathit{eff}}}{R_{\mathit{eff}}}$$

where $X_{\mathit{eff}}$ is the effective electrical reactance and $R_{\mathit{eff}}$ is the effective resistance. Given the equations, were:

$$R_{\mathit{eff}} = \frac{R_{par}}{(1 - \omega^2 LC_{par})^2 + (\omega C_{par} L_{par})^2}$$

$$X_{\mathit{eff}} = \frac{\omega(L - \omega^2 LC_{par} - C_{par} R_{par}^2)}{(1 - \omega^2 LC_{par})^2 + (\omega C_{par} L_{par})^2}$$

As the operating frequency increases, Rpar and Cpar also increase, thereby degrading the quality factor of the inductor. Since the parasitic capacitance is directly proportional to the dielectric constant of the material, replacing the higher dielectric constant material with air, having a dielectric constant of about 1, reduces the parasitic capacitance effects within the inductor and therefore increases the inductor's quality factor. Thus, by removing material therewithin, through the incorporation of the cavity 160, increases the quality factor of the inductor 125 of the present invention. As can be seen in FIG. 13, the inductor 125 of the present invention comprising the cavity 160 feature, particularly at frequencies greater than 1 GHz, exhibits a greater quality factor than the inductor 125 without such a feature.

The cavity 160 of the inductor 125 may also be used as a tuning mechanism. For example, when the multilayer inductor is used in a self-resonance mode, the self-resonance being achieved as a result of the interaction between its inductance and parasitic capacitance, the resonance frequency may be modified by fabricating a cavity comprising different volumes. Consider, for example, an inductor 125 built comprising a relatively high dielectric constant material (FIG. 13), where the permittivity of the material is about 70. By changing the cavity volume from nearly zero (having a self-resonance frequency of about 2.26 GHz), to the condition where the structure is fully enclosed in the material (self-resonance frequency ~1.9 GHz), a change in resonance frequency of about 15.9% is achieved. Furthermore, by incorporating a material having a higher dielectric constant in the inductor 125, the self-resonance frequency could increase from about 25 percent to about 50 percent depending on the specific material used. Thus, by modifying the volume of the cavity 160 and by incorporating different materials comprising different dielectric constants, the resulting resonance frequency may be tuned to a specific value or values (FIGS. 13A and 13B).

Figure 13A:
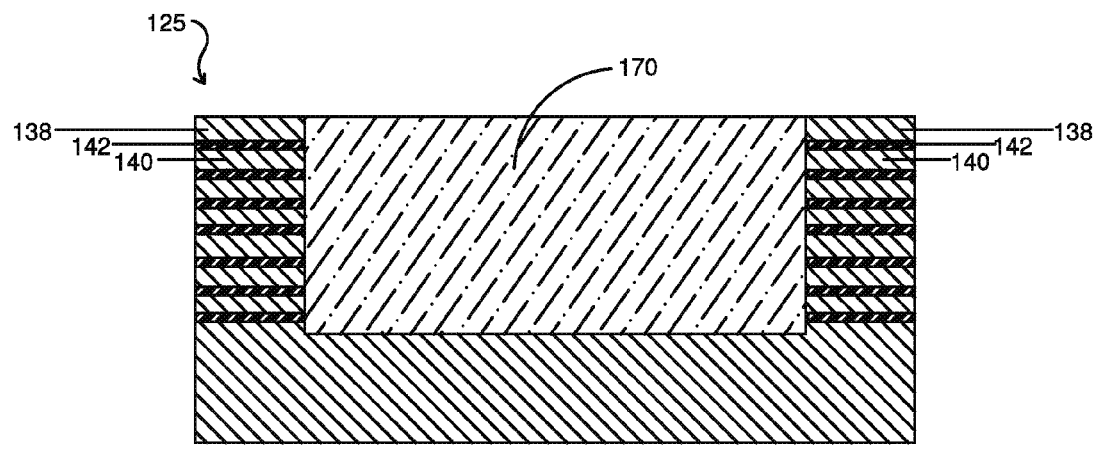
FIG. 13A illustrates a cross-sectional view of an embodiment of the inductor of the present invention comprising a cavity fill material.
Figure 13B:
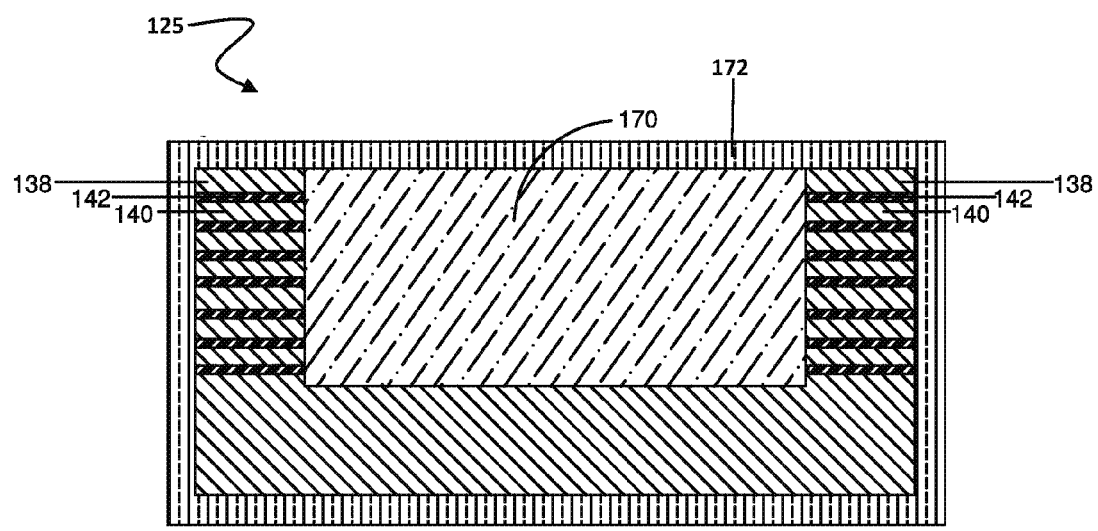
FIG. 13B illustrates a cross-sectional view of an embodiment of the inductor of the present invention comprising a cavity fill material and an encapsulation material.

FIGS. 13A and 13B illustrate cross-sectional views of embodiments of the MLMT inductor 125 of the present invention in which a cavity fill material 170 is used. As shown in this alternate embodiment, the cavity 160 of the MLMT inductor 125 is filled with a material designed to facilitate tuning of the inductance and/or the quality factor of the inductor 125. The cavity fill material 170 may comprise a metallic, a ceramic or a polymeric material. Specific examples may comprise a dielectric polymeric or ceramic material. Furthermore, the cavity fill material 170 may comprise ferromagnetic, ferroelectric, piezoelectric, paramagnetic or paraelectric materials.

As shown in the cross sectional view of FIG. 13B, the MLMT inductor 125 may be enclosed in an encapsulation material 172. Such encapsulation materials 170 may include a polymeric material such as polyimide, polyester or polyurethane. The encapsulation material 174 may be used with the MLMT inductor 125 having or not having the cavity 160 as well as an inductor 125 having or not having the encapsulation material 174.

Computer models of both an embodiment of the multilayer, multi-turn inductor of the present invention and a solenoidal wire wound air core inductor of the prior art were generated and compared. IE3D™ method of moments based electromagnetic simulation software, created by Mentor Graphics® of Wilsonville Oreg., was used to generate both models.

The computer models were based on an inductor with a nominal inductance of 39 nH operating at 50 MHz and 150 MHz. Model "A" represents the stated performance parameters in the manufacturer's datasheet of the prior art wire wound air inductor having a length of about 6.35 mm, a width of about 4.95 mm, a height of about 4.2 mm, and a self resonating frequency of between about 1.0 GHz to about 1.5 GHz.

A second model, model "B" was generated based on the structural characteristics of the multi-layer, multi-turn inductor 125 of the present invention. Like model "A", the second model "B" inductor 125 was designed with a nominal inductance of 39 nH. The second model inductor was designed with a length of about 6.35 mm, a width of about 4.95 mm a height of about 1.6 mm, and a self-resonance frequency of about 1.6 GHz. The difference in height is due to the compact, more efficient design of the multi-layer, multi-turn inductor of the present invention. The table shown below details the modeled electrical performance of the modeled inductors.

TABLE 3

| Frequency | Inductance | | Quality Factor | | Volume | |
| --- | --- | --- | --- | --- | --- | --- |
| | Model A | Model B | Model A | Model B | Model A | Model B |
| 50 MHz | 38 nH | 38 nH | 84.6 | 115 | 132 mm³ | 51 mm³ |
| 150 MHz | 39 nH | 38 nH | 135 | 169 | 132 mm³ | 51 mm³ |

As shown in table 3 above, the inductor 125 of the present invention comprises a quality factor that is greater than 100 operating at about 50 MHz and about 150 MHz at volume that is about 62 percent smaller than a wire wound, air core inductor of the prior art. More specifically, at an operating frequency of about 50 MHz, the inductor design of the present invention has a Q factor that is about 36 percent greater than the prior art and at an operating frequency of about 150 MHz, the multi-layer, multi-turn inductor 125 of the present invention has a Q factor that is about 25 percent greater than the prior art designed inductor. Thus, the multi-layer, multi-turn inductor 125 of the present invention operates at a much greater efficiency with a smaller volume than an air core wire wound inductor of the prior art.

As noted above, an inductor may exhibit parasitic effects. Associated with the inductor is a parasitic capacitance that is frequency dependent and whose contribution to the overall impedance increases with frequency. As a result of the parasitic capacitance, there exists a self-resonance frequency for the inductor beyond which the inductor behaves like a capacitor. To prevent the onset of parasitic capacitance, the inductor may be designed such that the inductance is nearly unchanging around the frequency of operation. Preferably, the slope of the reactance versus frequency graph is nearly linear (around the frequency of operation) with slope, $\partial X/\partial\omega \sim L$ (where X is the reactance, and L is the inductance that was designed for). Operating the inductor in this regime ensures that the parasitic coupling via electric fields is kept to a minimum. It is understood that that the X versus $\omega$ may not be perfectly linear due to other effects such as current crowding, proximity and skin effects.

Furthermore, high frequency devices, such as a circuit for wireless communications, often require tunable components residing therein. The MLMT inductor 125 of the present invention may be used as a circuit component within such a high frequency communication circuit, either to enable tenability of different frequency bands in a multi-band device, or to adapt to a change in an external stimulus, such as in a sensor.

In a preferred embodiment, the MLMT inductor 125 of the present invention may be tuned such that its inductance and/or its internal electrical resistance within the structure can be selectively adjusted or modified to produce a desired effect. In this preferred embodiment, the inductance and/or the quality factor may be selectively adjusted or tuned at a given frequency, frequencies or band of frequencies.

This tunability of the quality factor and/or the inductance may be accomplished manually or automatically, such as by an electrical means. In one embodiment, a trigger such as a change in the surrounding environment such as temperature, pressure, and the like, may elicit a change within the structure of the MLMT inductor 125 that selectively modifies the quality factor and/or the inductance of the inductor. This change within the MLMT structure may be the result of an electrical signal or a mechanical switch.

FIG. 14 illustrates an embodiment of a multi-layer multi-turn inductor 125 of the present invention. As illustrated, the exemplary multi-layer structure comprises four layers, a first layer 174, a second layer 176, a third layer 178, and a fourth layer 180 where each layer has one turn. Although the structure of the inductor 125 is illustrated having a curved cross-section, each layer 174, 176, 178, 180 comprising the inductor 125 structure may be constructed with a rectangular cross-section, a circular cross-section, a triangular cross-section, or may be constructed with a non-limiting polygon cross-section. Furthermore, the layers 174, 176, 178, 180 of the inductor 125 may be formed in a sinusoidal form, an irregular form or a "FIG. 8" form where the respective left and right sides of the inductor alternate to opposite sides. The inductor structure 125 further comprises at least one via 144 that electrically connects at least two layers.

In a preferred embodiment, each of the layers 174, 176, 178, 180 comprises at least one terminal. As shown, a first terminal 182 resides along the first layer 174, a second terminal 184 resides along the second layer 176, a third terminal 186 resides along the third layer 178 and a fourth terminal 188 resides along the forth layer 180. Each terminal 182, 184, 186, 188 is constructed such that a gap 189 resides between respective first and second ends 183, 185 of the layers. A via 144 is preferably positioned within the gap 189 providing electrical connection therebetween.

Figure 14B:
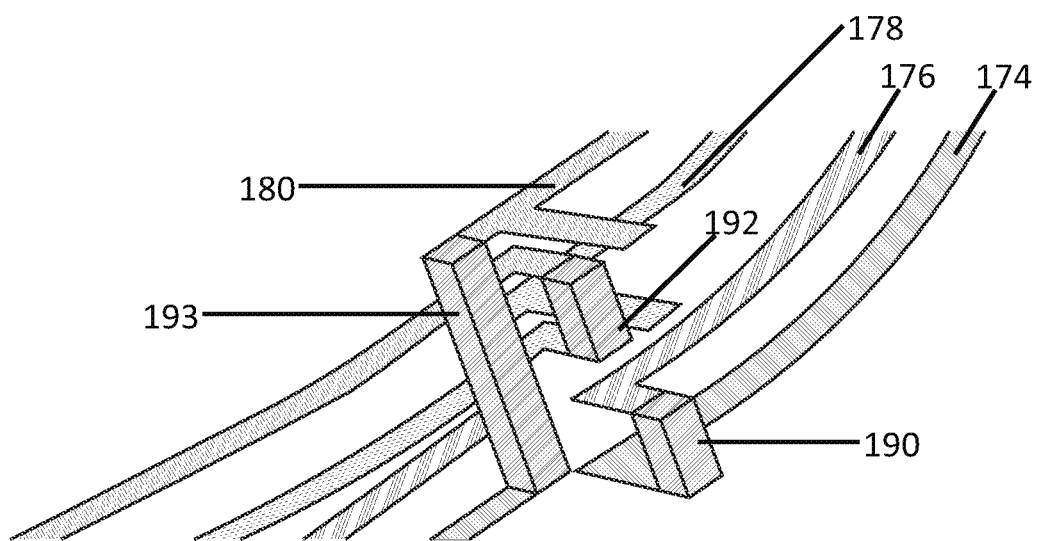
FIG. 14B illustrates a magnified view of an alternate embodiment of the terminal connections shown in FIG. 14.

As shown in FIG. 14B, a first via 190 is vertically positioned between the first layer 174 and the second layer 176, residing within the gaps of the first and second terminals 182, 184 providing electrical connection therebetween and thereby forming an "A" inductor structure of two layers. A second via 192 is vertically positioned between the third and the fourth layers 186, 188 residing within the gaps 189 of the third and fourth terminals 186, 188 providing an electrical connection therebetween, and thereby forming a "B" inductor structure of two layers. A third via 193 is vertically positioned along an inner surface of the layers providing electrical connection between the four layers.

In a preferred embodiment, the vias may be designed such that they provide a switchable electrical connection between the layers. The via switch positions may provide an electrically conducting or low electrical resistance connection between layers, a high electrical impedance connection, an electrical open, or an electrical short between layers. Thus by switching the electrical connection between layers, the electrical resistance within the inductor is modified. Therefore, the resulting inductance and quality factor of the resulting, "effective" inductor is selectively changed.

Figure 15:
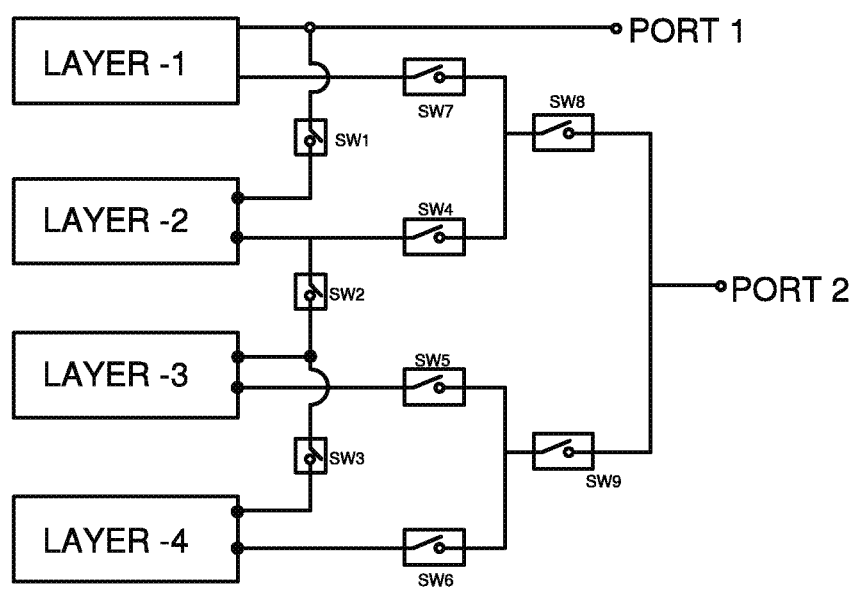
FIG. 15 shows an embodiment of a switching connection configuration utilized with the inductor of the present invention.

FIG. 15 shows an embodiment of a schematic illustrating various electrical switchable connections between the four layers of the inductor shown in FIG. 14. As illustrated, these switches, SW1-SW9, can be turned on and off manually or automatically, such as by a computer program, thereby providing a multi-layer, multi-turn tunable inductor structure 125 of the present invention. Table 4 shown below details the possible switchable configurations of the inductor embodiment illustrated in FIG. 15. It is noted that these connections and layer nomenclature are exemplary. The layers are interchangeable and dependent on the overall circuit fabrication process.

TABLE 4

| | Switches Open | Switches Closed |
|---|---|---|
| Conn 1 | SW 1, SW 2, SW 3, SW 4, SW 5, SW 6, SW 9 | SW 7, SW 8 |
| Conn 2 | SW 2, SW 3, SW 5, SW 6, SW 9 | SW 1, SW 4, SW 7, SW 8 |
| Conn 3 | SW 3, SW 6, SW 8 | SW 1, SW 2, SW 4, SW 5, SW 7, SW 9 |
| Conn 4 | SW 8 | SW 1, SW 2, SW 3, SW 4, SW 5, SW 6, SW 9 |

For example, given the embodied inductor shown in FIG. 14, with an outer radius of about 2 cm, a layer width of about 1 mm and a layer depth of about 100 um, the following inductance and quality factor values were measured for the 4 different switching connections, Conn 1, Conn 2, Conn3 and Conn 4 as detailed in Table 5 below.

TABLE 5

| | Conn 1 | | Conn 2 | | Conn 3 | | Conn 4 | |
|---|---|---|---|---|---|---|---|---|
| Freq | L (nH) | QF | L (nH) | QF | L (nH) | QF | L (nH) | QF |
| 500 KHz | 249 | 11.9 | 238.6 | 20.2 | 883.8 | 26.5 | 849 | 36.9 |
| 1 MHz | 247 | 19.8 | 236.8 | 31.4 | 879.2 | 42.6 | 845 | 58.1 |
| 2 MHz | 246 | 30.7 | 235.8 | 45.8 | 876.9 | 64 | 843.5 | 85.6 |

As shown by the measured values in Table 5 above, the ability to change the electrical connections within the tunable inductor 125 of the present invention, effectively changes the inductance and quality factors at the different operating frequencies.

Figure 16:
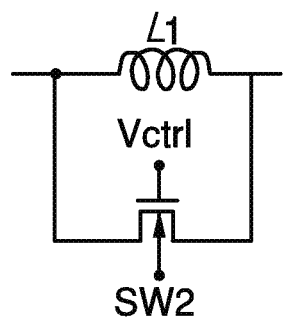
FIG. 16 illustrates an embodiment of a MOSFET switch utilized with the inductor of the present invention.
Figure 17:
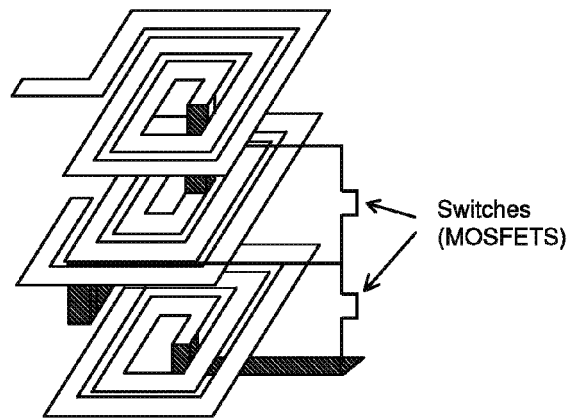
FIG. 17 shows an embodiment of multiple MOSFET switches utilized with the inductor of the present invention.

FIG. 16 illustrates another tuning embodiment of the inductor of the present invention. As shown, a metal oxide semiconductor field effect transistor (MOSFET) driven switch may be used to tune the multi-layer multi-turn inductor of the present invention. As shown in FIG. 17, multiple MOSFET switches may be used to turn selected layers of the inductor on and off.

In addition to the utilization of various switching embodiments, the incorporation of an alternate or a multitude of different materials comprising different dielectric constants may also be used to adjust or tune the inductance and quality factor of the inductor of the present invention. For example, the center or cavity 160 portion of the inductor may be filled with a polymeric material having a different dielectric constant than that of the metal layer and the dielectric insulating layer positioned between the conducting layers (FIGS. 13A and 13B).

In addition, alternate materials such as a piezoelectric or a pyroelectric material may also be incorporated within the structure of the multilayer multi turn inductor 125 of the present invention. For example, the piezoelectric or pyroelectric material may reside within the cavity 160 or alternatively comprise the insulator and/or conductor layers. A piezoelectric material typically generates an electrical voltage when a mechanical stress is applied to the material. A pyroelectric material generally generates an electrical voltage when the material is exposed to a change in temperature. Therefore, such materials could be incorporated within the structure, such as within a layer 126 or cavity 160, of the inductor 125 to provide the stimuli to tune or change the inductance and quality factor of the inductor 125. The impedance and/or quality factor of such an inductor 125 could be automatically adjusted if the environment, such as the surrounding temperature or pressure about the inductor changes.

The inductor 125 of the present invention can also be incorporated within various electrical circuits that operate at least at the radio frequency range of about 3 kHz. In a preferred embodiment, the multi-layer multi-turn inductor 125 can be electrically connected within an electrical circuit operating at about 1 MHz or greater. In particular, such electrical circuits that operate at these frequencies can, depending on the application, be designed to carry varying amounts of electrical current in a system processing different power levels. For example, some inductors used in RF circuits are rated to carry a maximum of about 0.5 A of current. Furthermore, other inductors may be rated to carry current levels that are less than 0.1 A or greater than 1 A. Typically power levels are driven by the load which can range from a few microwatts to a few watts. Additionally, inductors utilized in induction cooking systems typically have rated currents that exceed 1 to 2 A. Some inductors utilized in these induction cooking systems carry as much as 10-40A, which can transfer 3-8 kilowatts or more to the load.

Furthermore, an electrical circuit operating within these radio frequency ranges, may have an electrical power of at least 1 kWatt within the circuit. Furthermore, such electrical circuits incorporating the multi-layer, multi-turn inductor of the present invention may have 0.5 kilowatts or more of electrical power within. The multi-layer multi-turn inductor 125 and in particular, the multi-layer wire 104 of the present invention are designed to carry the increased electrical current and electrical power within the multiple layers.

Figure 18:
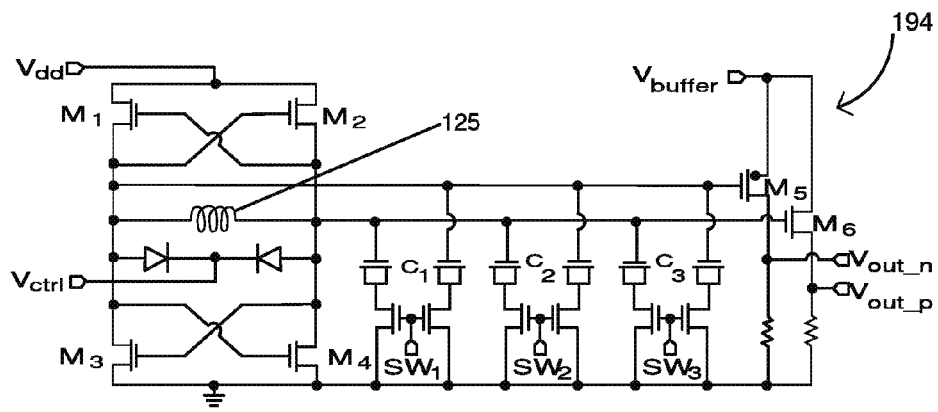
FIG. 18 illustrates an embodiment of a high frequency mixer electrical circuit incorporating the inductor of the present invention.

FIG. 18 illustrates an embodiment of an electrical circuit 194 comprising the inductor 125 of the present invention. Specifically, the electrical circuit 194 is an exemplary mixer circuit. A mixer circuit is an electrical circuit in which two or more electrical inputs are combined into one electrical output. In addition to electrical mixer circuits, the inductor 125 of the present invention may be electrically connected within other non-limiting electrical circuits that are designed to operate at least within the radio frequency range. In a preferred embodiment, the inductor 125 of the present invention may be electrically connected within an upconverting mixer circuit, a downconverting mixer circuit, modulators, demodulators, synthesizing circuits such as a PLL synthesizing circuit, amplifying and driver circuits, detecting circuits such as RF log detectors and RF RMS detectors, a wireless power circuit, positionable at either or both the transmitting or receiving side, transceivers and power controllers.

Such circuits incorporating the multi-layer multi-turn inductor 125 of the present invention, operating at or within the RF frequency range, may be used to charge an electrochemical cell within a motor vehicle such as an automobile, motorcycle, truck or the like. Furthermore, such electrical circuits incorporating the multi-layer, multi-turn inductor 125 may also be used for induction heating applications such as an inductive heating element of a stove, space heater or furnace.

Figure 19:
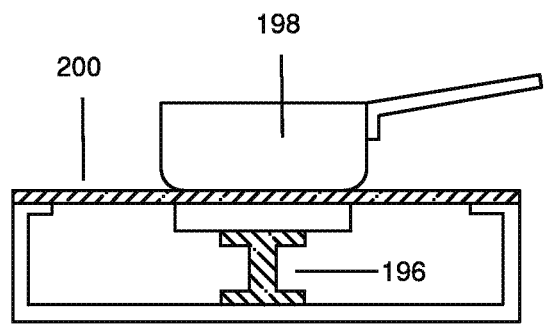
FIG. 19 shows a cross-sectional view of an embodiment of an induction heating element utilizing the inductor of the present invention.

FIG. 19 illustrates a cross-sectional view of an embodiment of a stovetop induction heating element 196 in which the inductor 125 of the present invention is incorporated therewithin. As shown, a cooking vessel 198 is positioned on the top surface of an induction heating surface 200. This surface 200 is comprised of a material that does not react in the presence of adjacent magnetic fields. The surface 200 is designed such that the temperature of the surface 200 does not increase thereby preventing the possibility of accidental burns or fire.

In this embodiment, an electric current flows through the MLMT inductor 125 which emits an oscillating magnetic field. The magnetic field produced by the inductor 125 interacts with the material (which in some cases may be ferromagnetic, of the cooking vessel 198. Such interaction increases the heat of the cooking vessel 198 which heats and cooks the food therein.

Figure 20:
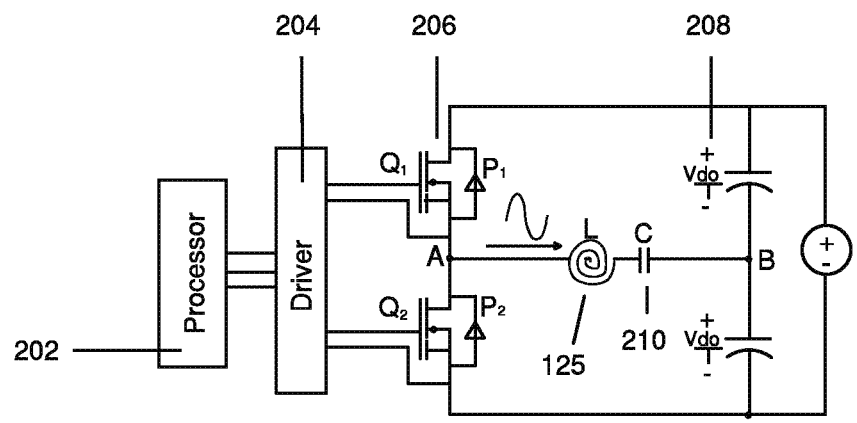
FIG. 20 illustrates an embodiment of an electrical circuit of an induction heating utilizing the inductor of the present invention.

In general, an induction heating system comprises an input power and power factor corrector, a rectifier and output filter, an inverter circuit, a load or resonant circuit and a control circuit. FIG. 20 illustrates an embodiment of an electrical circuit comprising the MLMT inductor 125 that is designed for use with an induction heating cooking element 196. As shown, the circuit comprises at least one computer processor 202, an electrical power driver 204, a power factor corrector 206, a rectifier 208, the MLMT inductor 125, and a capacitor 210.

Induction heating systems, such as the induction stove top heating element 196 shown in FIG. 19, in general provide efficient, high speed, low pollution producing heat. In particular, the MLMT inductor 125 of the present invention can be used in the KHz frequency range and unlike Litz wire induction heating elements of the prior art, can also be operated in the MHz frequency range. Thus by operating in the MHz frequency range, the MLMT inductor 125 provides an induction heating element that operates more efficiently with lower energy loss. In addition, cooking vessels 198 comprising copper and/or aluminum, such as a copper or aluminum base may also be used.

The present teachings also include a method of manufacturing the inductor after the inductor is designed. The multi-layer multi-turn inductor 125 may utilize strips of metal that may be deposited through a specific mask in, for example but not limited to, a PCB/ceramic/metal printing process or in a semiconductor foundry. An alternative method of fabricating the inductor may utilize conductive tape/ribbon/sheet/leaf with one or more tape/ribbon/sheet/leaf placed on top of each other separated by an insulating layer and shorting the multiple strips by soldering at the designated via locations. Another method of fabricating the inductor would be to cut out specific shapes from conductive sheets or "leaf" (for e.g.

gold or copper leaf) and following steps that similar to that for the conductive tape/ribbon. A three dimensional printing process (such as that offered by Eoplex Technologies) may also be used in addition to metal deposition processes like physical vapor deposition, thin film deposition and the like.

Figures 21, 22:
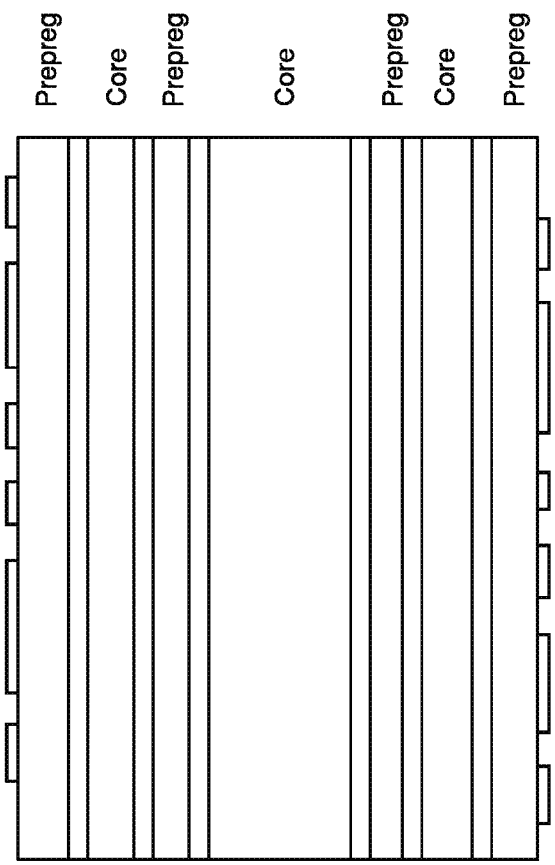
FIG. 21 illustrates an embodiment of the inductor of the present invention constructed with a printed circuit board stack up.
FIG. 22 shows a table of an embodiment of a fabrication stack up for a 6-layer PCB board as obtained from an established PCB manufacturer.

The present teachings lend itself to be incorporated with current fabrication techniques for multi-layer printed wiring board, printed circuit boards and semiconductor fabrication technologies with multi-layer interconnects as shown in FIG. 21. As advancements in fabrication techniques are made, it is expected that the multi-layer multi-turn inductor 125 will likely benefit greatly from such improvements. This compatibility with conventional fabrication techniques will allow these inductors to be relatively easily incorporated into conventional circuit boards. Such advances may also provide accurate repeatability and small feature sizes (i.e., high resolution).

The unique arrangement of the layers and customized wire segmentation in the present system compared with existing design technologies demonstrates improved system performance in similar and smaller packaging volumes as shown by quality factors that are more than two times higher than those realized from existing technologies. By combining material with specific properties, specifying shapes, lengths, and thicknesses and defining layer order, the present system permits pairing of the inductance and quality factor with a specific application to optimally achieve a desired response, including, but not limited to, electrical circuit operation, particularly high frequency RF electrical circuit operation, and increased electrical power and current carrying applications.

Another specific advantage of the present system is that it enables a more efficient means of Near Field Magnetic Coupling (NFMC) for power and/or data transfer in an equivalent or smaller design volume by reducing conductor loss associated with increasing frequencies (due to the phenomenon referred to as Skin Effect). The proposed system also provides a solution that can be relatively easily achieved by existing manufacturing techniques (for example multi-layer printed wiring board, FIG. 21), and can therefore be integrated with other circuit components such as ICs, resistors, capacitors, surface mount components, etc. Other advantages of the present system includes reducing power consumption thereby leading to longer battery lives (where applicable), a reduction in the Joule heating of the electrical circuit and/or device, decreasing the consumption of environmental resources of the appliance/device, and any other benefit derived from a more energy efficient device. Furthermore, such fabrication techniques provide miniaturization of the inductor 125 as shown in the example given in FIG. 22.

In addition, the present invention may be utilized in a system for multi-mode operations. Such a system may include an antenna of a multi-layer multi-turn structure as discussed in U.S. patent application Ser. Nos. 13/233,569, 13/233,538, 13/233,624, 13/233,663, 13/233,686, 13/233,729, 13/233,735, and 13/233,751, incorporated herein by reference.

Near Field Magnetically Coupled (NFMC) systems are becoming popular for uses in diverse applications, such as, for example, wireless power and Near Field Communication (NFC). To reduce size of systems, common RF circuit systems may be utilized with the ability to switch between modes.

For example, when designing for 13.56 MHz operation, an NFMC system may be designed to operate in at least two modes: (1) the wireless power mode, to transfer electrical power wirelessly and (2) an NFC mode that enables near field data transfer. Other modes of communication known to those of skill in the art are also possible.

In an embodiment, the present invention could be utilized in a radio frequency identification (RFID) system, wherein the additional NFC functionality could be included such that RFID sensors/transponders would be enabled to detect and communicate with other devices. Specifically, when designing for a lower frequency operation, i.e., in the 100-500 KHz range, the additional NFC mode could enable low frequency RFID detection and communication (for example 135 KHz). In addition, the system may also operate at higher frequencies. For example, the RFID system could operate in both wireless power and near field communication modes at a frequency of about 6.78 MHz.

In such a system, additional circuitry may be utilized to switch between the wireless power mode and communication mode(s). Furthermore, the antenna or RFID sensors/transponders may be designed such that they can be switched between wireless power transfer mode, NFC mode and/or another communication mode. The antenna or RFID sensor/transponder may or may not be comprised of an MLMT structure.

In another embodiment, a system for multi-band wireless power transfer and multi-band near field communication is also provided. This system may include an antenna or antennas, i.e. an MLMT antenna, enabled for multiband wireless power transfer and/or near field communication. In this embodiment, multiple wireless power frequency bands might be utilized for wireless electrical power transfer. In an example, frequencies within in the ranges 100 to 500 KHz, 6.5 MHz to 7 MHz, and 13 MHz to 14 MHz may be utilized. However, it is recognized these frequency ranges are for illustration purposes and should not be considered limiting. Other frequency ranges may also be utilized.

Thus, it is contemplated that by using a multi-layer multi-turn antenna, for multi-mode multi-band wireless power transfer and/or near field communication, several benefits are possible. These benefits include, for example, interoperability across various protocols and versatility among various electrical circuitries and systems. Furthermore, since the system incorporates the multi-layer multi-turn structure of the present invention, the system requires less space in a device due to its compact efficient structure and circuitry. In addition, the multi-turn multi-layer structure is cost effective to manufacture. Moreover, such systems may include additional circuitry for further enablement of features such as mode switching, tuning, and/or interference mitigation among others.

It is noted however, that the inductive antenna structure utilized in the system, may or may not be of the MLMT type. In either case, the antenna should be designed such that it is capable of switching between different frequency bands for wireless power transfer and/or near field communication. Such switching can be achieved utilizing tuning techniques discussed above or other switching or tuning techniques known in the art.

Other applications that may benefit from these electrical circuits comprising the MLMT inductor 125 of the present invention include includes but are not limited to geo-sensing, oil exploration, fault detection, transportation, consumer electronics, portable electronics, military, defense and medical devices, among other medical implantable, medical non-implantable, commercial, military, aerospace, industrial and other electronic equipment or device applications. It is understood that the scope of the invention covers not only any application that will benefit from increases in efficiency, but also any application that may require the use of an inductive element.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. An electrical system, comprising:
   a) an electrical power source;
   b) a control circuit electrically connected to the electrical power source;
   c) a first circuit electrically connected to the control circuit, the first circuit comprising an inductor, comprising:
      i) a first conductor layer;
      ii) a second conductor layer spaced apart from the first conductor layer, the first conductor layer and the second conductor layer being electrically conductive;
      iii) an insulator layer positioned in the space between the first conductor layer and the second conductor layer; and
   d) wherein when an electrical current, supplied by the electrical power source, is propagated within at least the first conductor layer a magnetic flux is generated within the inductor; and
   e) wherein when a change in at least one of a frequency, a magnitude, or a waveform shape of the propagated electrical current causes an inductance to be generated.

2. The electrical system of claim 1 wherein an electromotive force is generated when at least one of the frequency, the magnitude, or the waveform shape is changed.

3. The electrical system of claim 1 wherein a magnitude of the magnetic flux is proportional to the amount of change of at least one of the frequency, the magnitude, or the waveform shape of the electrical current.

4. The electrical system of claim 1 wherein, an electrical resistance of at least one of the first conductor layer or the second conductor layer is reducable when a cross-sectional area of a conducting skin depth within at least the first conductor layer or the second conductor layer is increased, wherein the increased cross-sectional area is a result of electrically connecting at least a third conductor layer to the second conductor layer, a second insulator layer positioned therebetween.

5. The electrical system of claim 1 wherein a thickness of the first conductor layer is about equal to a thickness of a skin depth of the first conductor layer at a given frequency.

6. The electrical system of claim 1 wherein a thickness of the first conductor ranges from about 1.25 times to about 4 times a thickness of a skin depth of the first conductor layer at a given frequency.

7. The electrical system of claim 1 wherein a thickness of the second conductor ranges from about 1.25 times to about 4 times a thickness of a skin depth of the second conductor layer at a given frequency.

8. The electrical system of claim 1 wherein a first conductor layer thickness is about the same as a second conductor layer thickness.

9. The electrical system of claim 1 wherein a first conductor layer thickness is different from a second conductor layer thickness.

10. The electrical system of claim 1 wherein a thickness of a first skin depth of the first conductor layer is about the same as a thickness of a second skin depth of the second conductor layer.

11. The electrical system of claim 1 wherein a thickness of a first skin depth of the first conductor layer is different than a thickness of a second skin depth of the second conductor layer.

12. The electrical system of claim 1 wherein a thickness of the insulating layer is less than about 5 cm.

13. The electrical system of claim 1 wherein the inductor has an inductor quality factor greater than about 5.

14. The electrical system of claim 13 wherein the inductor quality factor is defined by the equation $$Q = \frac{2\pi f L}{R}$$

where f is the frequency of operation, L is the inductance, and R is the total ohmic and radiative resistance.

15. The electrical system of claim 1 wherein the inductor is capable of operating at an inductor frequency of at least 3 kHz.

16. The electrical system of claim 1 wherein at least one of the first and second conductor layers is formed from a thermally conductive material.

17. The electrical system of claim 1 wherein at least one connector electrically connects the first conductor layer and the second conductor layer electrically in parallel or series.

18. The electrical system of claim 17 wherein the connector is selected from the group consisting of a via, a solder, a tab, a wire, a pin, a rivet, a filled mesh structure, a conductive polymer, a conductive composite, a conductive adhesive, a liquid metal, a foamed metal, and combinations thereof.

19. The electrical system of claim 1 wherein the first conductor layer and the second conductor layer form a structure in which the first and second conductor layers are positioned in about a parallel orientation, a perpendicular, or at an angular relationship therebetween.

20. The electrical system of claim 1 comprising a third conductor layer and a fourth conductor layer electrically connected in parallel wherein the first and second conductive layers are connected electrically in parallel and are further connected electrically in series with the third and fourth conductor layer.

21. The electrical system of claim 1 wherein the inductor is electrically connectable with a second electrical circuit operating at about 100 kHz or greater.

22. The electrical system of claim 21 wherein the first electrical circuit is selected from the group consisting of a mixer circuit, an impedance matching circuit, an upconverting mixer circuit, a downconverting mixer circuit, a modulator, a demodulator, a synthesizing circuit, a PLL synthesizing circuit, an amplifying circuit, an electrical driver circuit, an electrical detecting circuit, an RF log detector, an RF RMS detector, an electrical transceiver, a power controller, and combinations thereof.

23. The electrical system of claim 1 wherein the inductor is electrically connectable within an induction heating circuit.

24. The electrical system of claim 1 wherein a second control circuit is electrically connectable to the inductor.

25. The electrical system of claim 1 wherein at least the first and second conductor layers has at least a partial revolution.

26. The electrical system of claim 1 wherein the first conductor layer or the second conductor layer comprises a material selected from the group consisting of copper, titanium, platinum, platinum and iridium alloys, tantalum, niobium, zirconium, hafnium, nitinol, cobalt-chromium-nickel alloys, stainless steel, gold, a gold alloy, palladium, carbon, silver, a noble metal, a conductive polymer, a conductive adhesive, a conductive composite, a liquid metal, a foamed metal, a conductive tape, a conductive ribbon, a conductive foil, a conductive leaf, a wire, a deposited metal, a biocompatible material, and combinations thereof.

27. The electrical system of claim 1 wherein at least one insulator layer is formed from an electrically insulative material.

28. The electrical system of claim 1 wherein the insulator layer comprises an electrically insulative material selected from the group consisting of air, polystyrene, silicon dioxide, a biocompatible ceramic, a conductive dielectric material, a non-conductive dielectric material, a piezoelectric material, a pyroelectric material, a ferrite material, and combinations thereof.

29. The electrical system of claim 1 wherein the system is capable of operating at an electrical circuit frequency of at least 3 kHz.

30. The electrical system of claim 1 wherein a microprocessor electronically controls the control circuit.

31. The electrical system of claim 1 wherein the system is operatable at an electrical circuit frequency or frequencies of at least 10 MHz.

32. An electrical system, comprising:
a) an electrical power source;
b) a control circuit electrically connected to the electrical power source;
c) a first circuit electrically connected to the control circuit, the first circuit comprising a first inductor, comprising:
  i) a first conductor layer and a second conductor layer spaced apart from the first conductor layer, the first conductor layer and the second conductor layer being electrically conductive;
  ii) a first insulator layer positioned in the space between the first conductor layer and the second conductor layers;
  iii) a first connector electrically connecting the first conductor layer and the second conductor layer electrically in parallel;
d) a second inductor electrically connected to the control circuit, the second inductor comprising:
  i) a third conductor layer and a fourth conductor layer spaced apart from the third conductor layer, the third conductor layer and the fourth conductor layer being electrically conductive;
  ii) a second insulator layer positioned in the space between the third conductor layer and the fourth conductor layers; and
  iii) a second connector electrically connecting the third conductor layer and the fourth conductor layer electrically in parallel, wherein the first inductor is electrically connected in series or parallel to the second inductor;
e) wherein when an electrical current, supplied by the electrical power source, is propagated within at least the first conductor layer, a magnetic flux is generated within the first inductor and/or the second inductor; and
f) wherein when a change in at least one of a frequency, a magnitude, or a waveform shape of the propagated electrical current causes an inductance to be generated within the first inductor and/or the second inductor.

33. The inductor of claim 32 wherein the first conductor and the second inductor are oriented so that the first and second inductors are positioned about parallel, about perpendicular, or at an angular relationship therebetween.

* * * * *